(12) United States Patent
Haddad et al.

(10) Patent No.: US 7,220,727 B2
(45) Date of Patent: May 22, 2007

(54) AMINOGLYCOSIDES AS ANTIBIOTICS

(75) Inventors: Jalal Haddad, Detroit, MI (US); Lakshmi Kotra, Detroit, MI (US); Shahriar Mobashery, Granger, IN (US)

(73) Assignee: Wayne State University, Detroit, MI (US)

( * ) Notice: Subject to any disclaimer, the term of this patent is extended or adjusted under 35 U.S.C. 154(b) by 315 days.

(21) Appl. No.: 10/415,732

(22) PCT Filed: Nov. 1, 2001

(86) PCT No.: PCT/US01/45639

§ 371 (c)(1),
(2), (4) Date: Feb. 19, 2004

(87) PCT Pub. No.: WO02/057281

PCT Pub. Date: Jul. 25, 2002

(65) Prior Publication Data

US 2005/0171035 A1    Aug. 4, 2005

Related U.S. Application Data

(60) Provisional application No. 60/245,051, filed on Nov. 1, 2000.

(51) Int. Cl.
| | |
|---|---|
| *C07H 15/00* | (2006.01) |
| *C07H 17/00* | (2006.01) |
| *C07H 23/00* | (2006.01) |
| *A01N 43/04* | (2006.01) |
| *A61K 31/70* | (2006.01) |

(52) U.S. Cl. .............................. 514/36; 514/25; 514/35; 536/16.8; 536/17.2; 536/17.5; 536/17.6; 536/17.9

(58) Field of Classification Search ............... 536/16.8, 536/17.2, 17.5, 17.6, 17.9; 514/25, 35, 36
See application file for complete search history.

(56) References Cited

U.S. PATENT DOCUMENTS 3,948,882 A * 4/1976 Umezawa et al. ......... 536/16.6
4,008,362 A * 2/1977 Akita et al. ................ 536/16.6

OTHER PUBLICATIONS

Goodman & Gilman's: The Pharmacological Basis of Therapeutics, 10th Edition, McGraw-Hill Medical Publishing Division, 2001, pp. 54-56.*
Gov et al., Peptides, 2001, 22:1609-1620.*
Balaban et al., Peptides 2000, 21:1301-1311.*
Ghiselli et al., Eur. J. Vasc. Endovasc. Surg., 2004, 27:603-607.*
Haddad, J. , et al., "Design of Novel Antibiotics that Bind to the Ribosomal Acyltransfer Site", *J. Am. Chem. Soc.*, 124, (2002),3229-3237.
Kuwahara, R. , et al., "Synthesis of Dibekacin Analogs Containing 3-oxa-and 3-aza-2,3,4-trideoxy-D-glycero-hexopyranose", *Carbohydrate Research*, 293, (1996), 15-30.

* cited by examiner

*Primary Examiner*—Shaojia Anna Jiang
*Assistant Examiner*—Traviss McIntosh
(74) *Attorney, Agent, or Firm*—Schwegman, Lundberg, Woessner & Kluth

(57) ABSTRACT

The present invention provides aminoglycosides and pharmaceutical compositions that include the aminoglycosides. The aminogylcosides are useful to treat or prevent infectious diseases (e.g., bacterial infections) in a mammal (e.g., human).

36 Claims, 13 Drawing Sheets

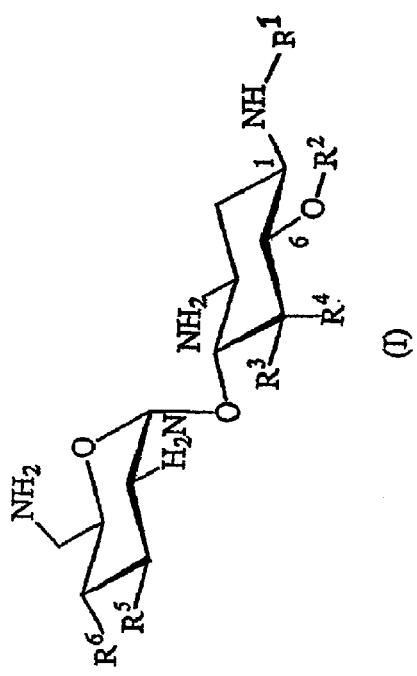
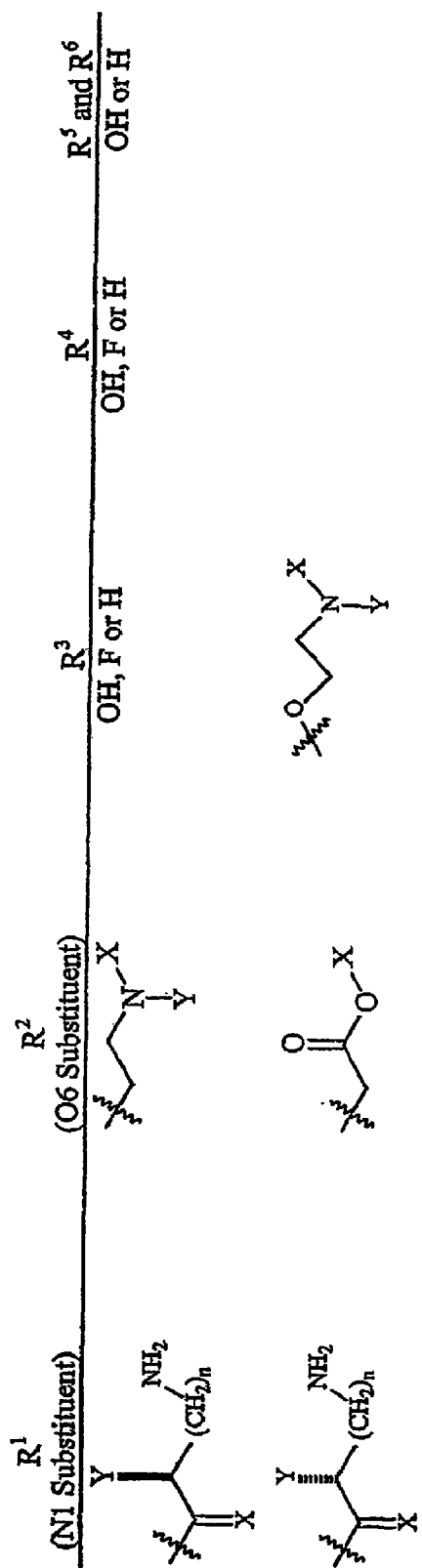
Fig. 1

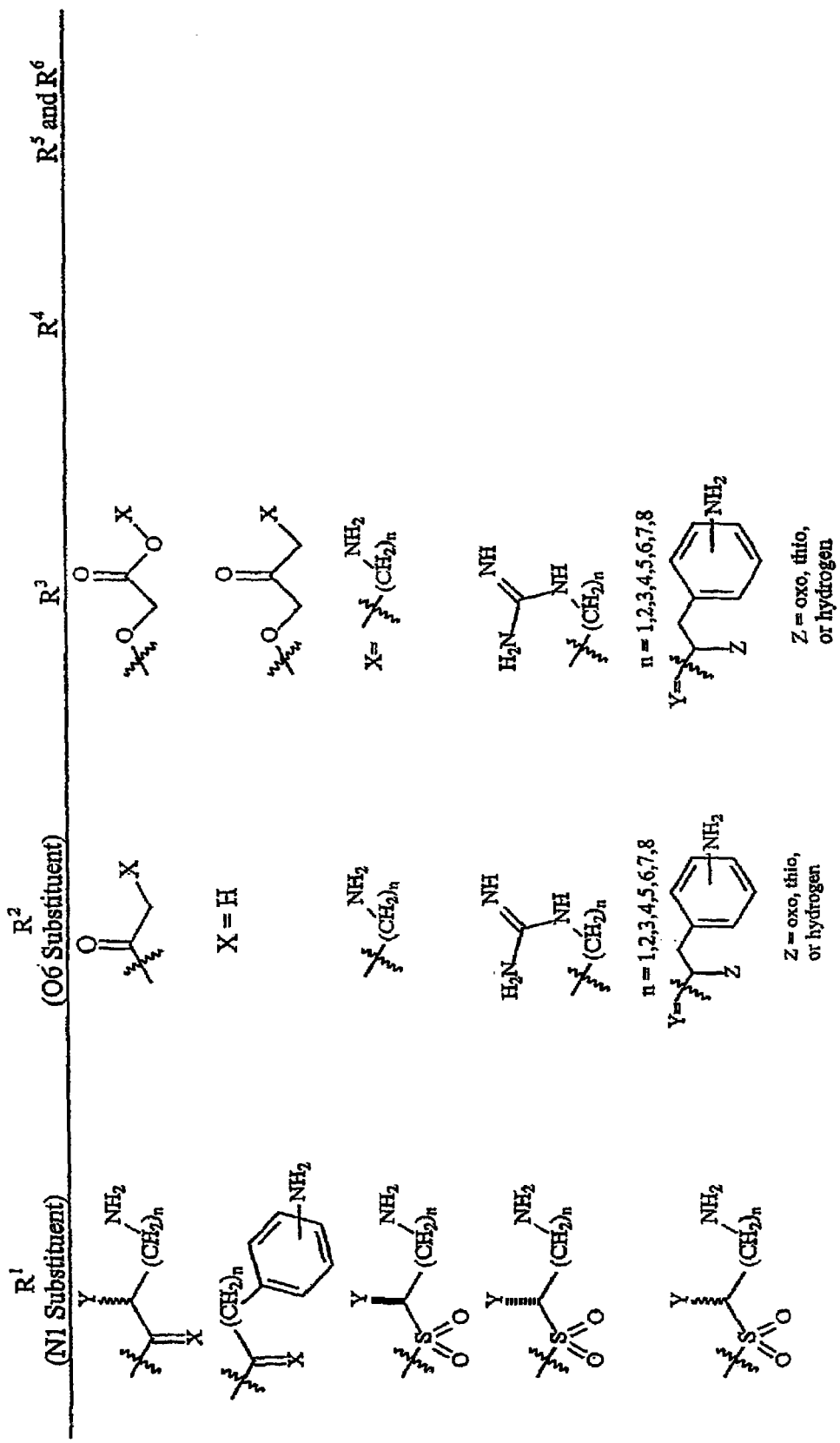

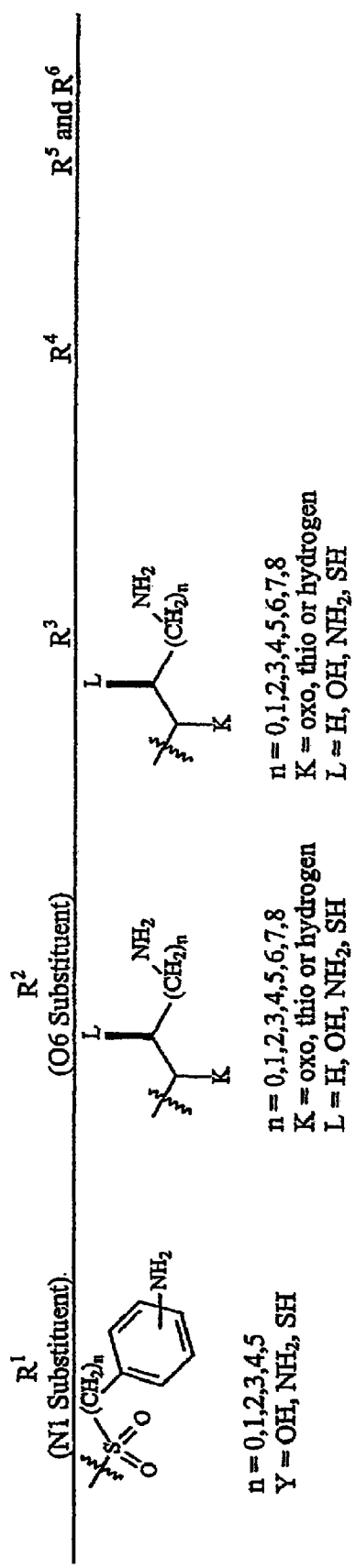

Fig. 2
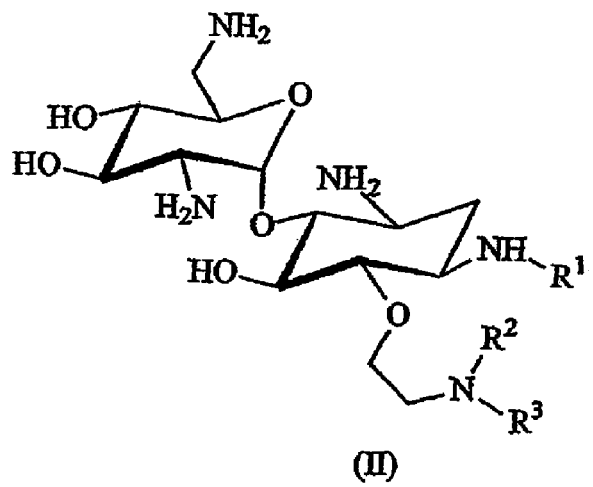
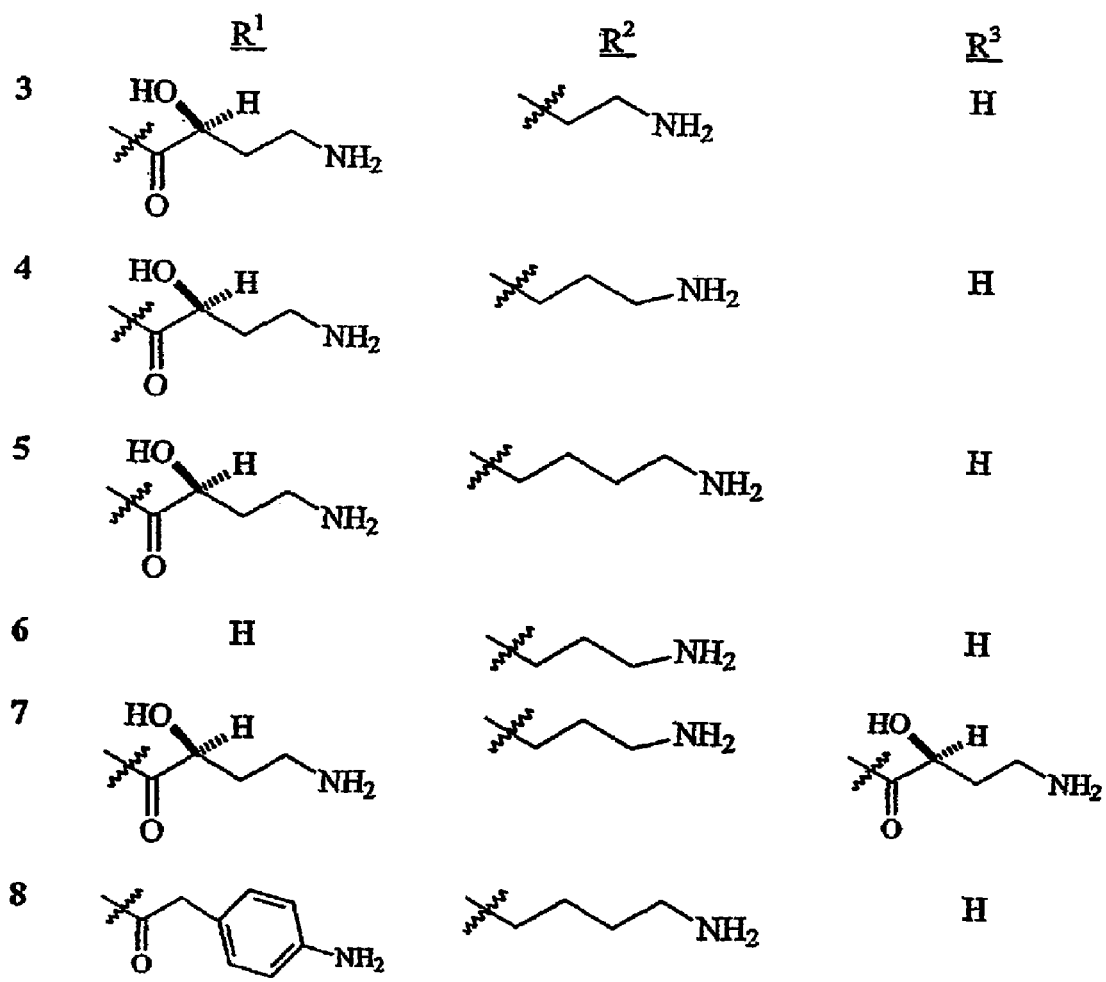

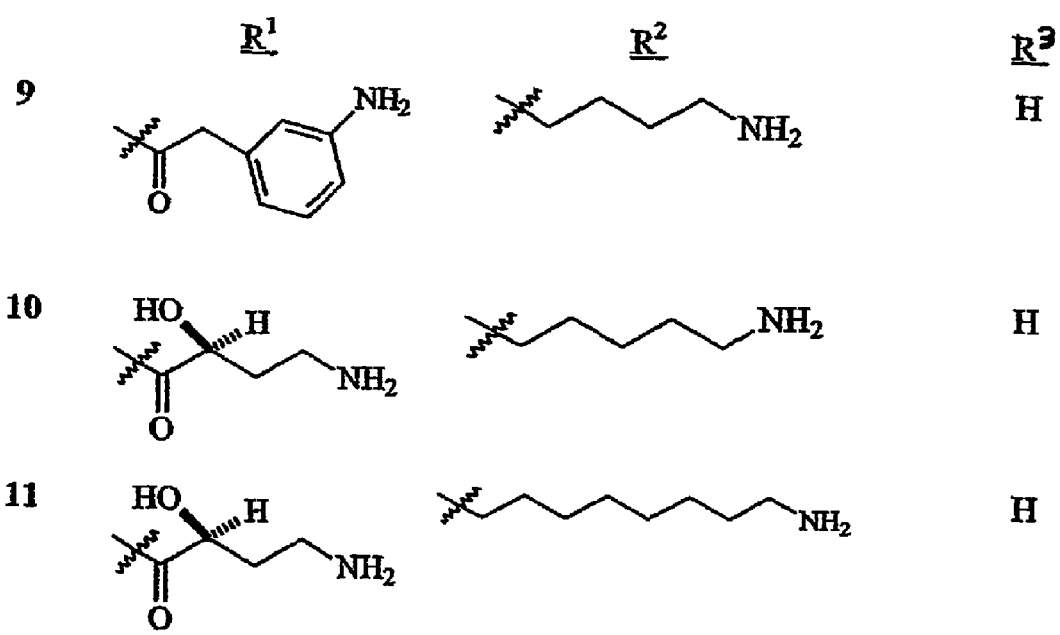

Reagents and conditions: (a) PhCH$_2$CO$_2$Cl, Na$_2$CO$_3$, acetone-water, 95%; (b) 1,1-dimetoxycyclohexane, TsOH, DMF, 87%; (c) MOMCl, Bu$_4$NI, (i-Pr)$_2$NEt, 32°C, 79%; (d) AcOH, dioxane-water, 60°C, 95%; (e) NaH, DMF, 89%; (f) TESCl, imidazole, DMAP, 80%; (g) (Boc)$_2$O, Et$_3$N, DMAP, 96%; (h) TBAF, THF, 85%; (i) MOMCl, Bu$_4$NI, (i-Pr)$_2$NEt, 32°C, 97%; (j) LiOH, dioxane, 88%; (k) CH$_2$=CHCH$_2$Br, Bu$_4$NI, (Me$_3$Si)$_2$NLi, 69%.

Reagents and conditions: (a) (i) O₃, CH₂Cl₂, (ii) Ph₃P, 81%; (b) CbzHN(CH₂)ₙNH₂, NaBH₃CN, AcOH, MeOH, 55-67%; (c) 1.3 N HCl, MeOH-CHCl₃, 73-87%; (d) NaHCO₃, THF-water, 46-54%; (e) 1,4-cyclohexadiene, Pd-C, AcOH, 51-68%.

Reagents and conditions: (a) PhCH$_2$CO$_2$Cl, Na$_2$CO$_3$, acetone-water, 89%; (b) N-hydroxysuccinimide, DCC, THF; (c) PhCH$_2$CO$_2$Cl, NaOH, acetone-water, 91%.

35 R = COCH₂-C₆H₄-p-NHCbz
36 R = COCH₂-C₆H₄-m-NHCbz

Reagents and conditions: (a) Pyridine, 42%; (b) 1,4-cyclohexadiene, Pd-C, AcOH, 52%. (c) NaHCO₃, THF-water, 74-75%; (d) condition b, 56-63%.

Figure 8

Table 1. Minimum inhibitory concentrations (MICs) of antibiotics against various bacterial strains.

| Bacterial strains | MIC (µg/mL) | | | | | | | | | |
|---|---|---|---|---|---|---|---|---|---|---|
| | KAN | GEN | TOB | AMP | CAZ | IMI | 3 | 4 | 5 | 6 |
| Escherichia coli JM83 | 64 | 4 | <1 | 1 | 4 | 0.03 | 0.06 | 8 | 2 | 1 | 32 |
| E. coli JM83 (APH(3')-I) | 8,000 | 2,000 | <1 | 1 | 16,000 | 0.5 | 0.25 | 32 | 8 | 8 | >512 |
| E. coli JM83 (AAC6'/APH2") | 2,000 | 500 | 64 | 128 | 8,000 | 0.5 | 2 | 32 | 8 | 8 | >512 |
| Serratia marcescens ATCC13880 | 16 | 8 | 4 | 16 | 32 | 0.25 | 0.5 | 32 | 8 | 4 | 64 |
| Enterobacter cloacae ATCC 3047 | 64 | 8 | 2 | 4 | 1,000 | 2 | 0.5 | 8 | 2 | 2 | 16 |
| Pseudomonas aeruginosa 500 66 | 32 | >128 | 2 | 4 | >500 | 64 | 0.25 | 8 | 2 | 2 | >512 |
| P. aeruginosa C43 | 4,000 | 1,000 | 16 | 4 | 32 | >500 | 128 | 32 | 64 | 4 | 2 | >512 |
| Staphylococcus aureus 3 | 64 | 4 | <1 | <1 | 4 | 2 | <0.03 | 2 | 0.5 | 0.5 | 4 |
| Enterococcus faecium 119 | 1,000 | 64 | 8 | 32 | 1 | >128 | 0.5 | 256 | 32 | 32 | >512 |

KAN, kanamycin; GEN, gentamicin; TOB, tobramycin; AMK, amikacin; AMP, ampicillin; CAZ, ceftazidime; IMI, imipenem.

Figure 9

Table 2. Kinetic parameters for turnover of compounds 4, 5, 8, 9, neamine, amikacin, and kanamycin A by APH(3')-IIa and the bifunctional enzyme AAC(6')/APH(2'').[a]

| | APH(3')-IIa | | | BF [APH(2'')] | | | BF [AAC(6')] | | |
|---|---|---|---|---|---|---|---|---|---|
| compound | $K_m$ (μM) | $k_{cat}$ (s$^{-1}$) | $k_{cat}/K_m$ (M$^{-1}$s$^{-1}$) | $K_m$ (μM) | $k_{cat}$ (s$^{-1}$) | $k_{cat}/K_m$ (M$^{-1}$s$^{-1}$) | $K_m$ (μM) | $k_{cat}$ (s$^{-1}$) | $k_{cat}/K_m$ (M$^{-1}$s$^{-1}$) |
| 4 | 81 ± 12 | 2.2 ± 0.2 | (2.7 ± 0.2) × 10$^4$ | 209 ± 32 | (2.5 ± 1.2) × 10$^{-3}$ | 12.0 ± 0.5 | 563 ± 120 | 2.1 ± 0.4 | (3.7 ± 0.3) × 10$^3$ |
| 5 | 22 ± 9 | 0.9 ± 0.2 | (4.0 ± 0.5) × 10$^4$ | 108 ± 20 | (1.6 ± 0.8) × 10$^{-3}$ | 14.0 ± 0.5 | 627 ± 138 | 4.2 ± 1.7 | 6.7 ± 0.5) × 10$^3$ |
| 8 | 49 ± 18 | 0.9 ± 0.2 | (1.8 ± 0.4) × 10$^4$ | 161 ± 19 | (1.3 ± 0.6) × 10$^{-3}$ | 8.1 ± 0.5 | 489 ± 95 | 4.0 ± 1.2 | (8.2 ± 0.4) × 10$^3$ |
| 9 | 33 ± 9 | 0.4 ± 0.1 | (1.2 ± 0.4) × 10$^4$ | 108 ± 18 | (1.6 ± 0.2) × 10$^{-3}$ | 14.0 ± 0.2 | 520 ± 37 | 3.7 ± 0.9 | (7.1 ± 0.2) × 10$^3$ |
| neamine (1) | 1 | 29 | 2.9 × 10$^7$ | 36 ± 2 | (6.8 ± 0.8) × 10$^{-3}$ | 189.0 ± 0.1 | 10 ± 3 | 4.3 ± 0.7 | (4.3 ± 0.3) × 10$^5$ |
| amikacin (2) | 53 | 2 | 3.8 × 10$^4$ | 299 ± 1 | 105 ± 9 | (3.5 ± 0.1) × 10$^5$ | 477 ± 14 | 4.1 ± 0.2 | (8.6 ± 0.6) × 10$^3$ |
| kanamycin | 3.1 ± 0.5 | 0.65 ± 0.02 | (2.1 ± 0.4) × 10$^5$ | 24 ± 2 | 177 ± 19 | (7.4 ± 0.9) × 10$^6$ | 4.5 ± 0.1 | 0.4 ± 0.4 | (8.9 ± 2.2) × 10$^4$ |

[a] The turnover data for amikacin and neamine with APH(3')-IIa (Siregar, J. J.; Lerner, S. A.; Mobashery, S. *Antimicrob. Agents Chemother.* 1994, *38*, 641), those for amikacin and kanamycin with the bifunctional enzyme (Azucena, E.; Grapsas, I.; Mobashery, S. *J Am. Chem. Soc.* 1997, *119*, 2317), and for kanamycin with APH(3')-IIa (*J. Am. Chem. Soc.* 1999, *121*, 11922-11923) have been reported.

AMINOGLYCOSIDES AS ANTIBIOTICS

CROSS-REFERENCE TO RELATED APPLICATIONS

This application is a U.S. National Stage application under 35 U.S.C. 371 from International Application No. PCT/US01/45696 filed 1 Nov. 2001 and published in English as WO 02/057281 on 25 Jul. 2002, which claimed priority under 35 U.S.C. 119(e) from U.S. Provisional Application Ser. No. 60/245,051 filed 1 November 2000, which applications and publication are incorporated herein by reference.

BACKGROUND OF THE INVENTION

Antibiotics are low-molecular weight antimicrobial agents that are produced as secondary metabolites by microorganisms that inhabit soil. For instance, Penicillium and Cephalosporium produce beta-lactam antibiotics (e.g., penicillin, cephalosporin, and their relatives). Actinomycetes (e.g., the Streptomyces species) produce tetracyclines, aminoglycosides (e.g., streptomycin and its analogs), macrolides (e.g., erythromycin and its analogs), chloramphenicol, ivermectin, rifamycins, and most other clinically-useful antibiotics that are not beta-lactams. Bacillus species (e.g., B. polymyxa and Bacillus subtilis) produce polypeptide antibiotics (e.g. polymyxin and bacitracin), while B. cereus produces zwittermicin.

The modern era of antibiotic therapy began with Fleming's 1929 discovery of penicillin, and Domagk's 1935 discovery of synthetic sulfonamides. Spurred by the need for antibacterial drugs during World War II, penicillin was isolated, purified and injected into experimental animals. The substance was found to not only cure infections, but also to possess low toxicity. This finding marked the beginning of the era of antibiotic use in human drug therapy and the intense search for similar antimicrobial agents of low toxicity that could be used to treat infectious diseases. The rapid isolation of streptomycin, chloramphenicol and tetracycline followed, and these and several other antibiotics were in clinical usage by the 1950's.

Antibiotics are used therapeutically to treat bacterial infections. Several types of antibiotics, classified according to their mechanism of action, are currently employed. The known types of antibiotics include, e.g., cell wall synthesis inhibitors, cell membrane inhibitors, protein synthesis inhibitors, and inhibitors that bind to or affect the synthesis of DNA or RNA.

Cell wall synthesis inhibitors, such as beta lactam antibiotics, generally inhibit some step in the synthesis of bacterial peptidoglycan. Penicillin is generally effective against non-resistant streptococcus, gonococcus and staphylococcus. Amoxycillin and Ampicillin have broadened spectra against Gram-negative bacterias. Cephalosporins are generally used as penicillin substitutes, against Gram-negative bacteria, and in surgical prophylaxis. Monobactams are generally useful for the treatment of allergic individuals.

Cell membrane inhibitors disorganize the structure or inhibit the function of bacterial membranes. Polymyxin, produced by Bacillus polymyxis, is a cell membrane inhibitor that is effective mainly against Gram-negative bacteria and is usually limited to topical usage.

Protein synthesis inhibitors include the tetracyclines, chloramphenicol, the macrolides (e.g. erythromycin) and the aminoglycosides (e.g. streptomycin). Aminoglycosides have been used against a wide variety of bacterial infections caused by Gram-positive and Gram-negative bacteria. Aminoglycosides bind to the bacterial RNA in manifestation of their activity. Davis, B. D. *Microbiol. Rev.* 1987, 51, 341–350. Mingeot-Leclercq, M.-P.; Glupczynski, Y.; Tulkens, P. M. *Antimicrob. Agents Chemother.* 1999, 43, 727–737. Moazed, D.; Noller, H. F. *Nature* 1987, 327, 389–394. Shaw, K. J., Rather, P. N.; Hare, R. S.; Miller, G. H. *Microbiol. Rev.* 1993, 57, 138–163. Streptomycin has been used extensively as a primary drug in the treatment of tuberculosis. Gentamicin is active against many strains of Gram-positive and Gram-negative bacteria, including some strains of *Pseudomonas aeruginosa*. Kanamycin is active at low concentrations against many Gram-positive bacteria, including penicillin-resistant staphylococci.

The structures of two aminoglycoside antibiotics, paromomycin and gentamicin $C_{1a}$, bound to the template sequences of ribosomal RNA (rRNA), have been determined recently by NMR. Fourmy, D.; Recht, M. I.; Blanchard, S. C.; Puglisi, J. D. *Science* 1996, 274, 1367–1371; (a) Fourmy, D.; Recht, M. I.; Puglisi J. D. *J. Mol. Biol.* 1998, 277, 347–362; (b) Fourmy, D.; Yoshizawa, S.; Puglisi, J. D. *J. Mol. Biol.* 1998, 277, 333–345; (c) Recht, M. I.; Fourmy, D.; Blanchard, S. C.; Dahlquist, K. D.; Puglisi, J. D. *J. Mol. Biol.* 1996, 262, 421–436; (d) Yoshizawa, S.; Fourmy, D.; Puglisi, J. D. *EMBO J.* 1998, 17, 6437–6448. These and other studies show that the neamine-class of aminoglycosides bind specifically to the A-site region on the 16S subunit of rRNA. Hence, neamine serves as a minimal structural motif for such binding. Fourmy, D.; Recht, M. I.; Blanchard, S. C.; Puglisi, J. D. *Science* 1996, 274, 1367–1371; Kotra, L. P.; Haddad, J.; Mobashery, S. *Antimicrob. Agents Chemother.* 2000 (in press)). As such, aminoglycosides are a suitable class of compounds that could be effective antibiotics.

Neamine itself is a poor antibiotic and is not clinically useful. However, clinically useful aminoglycosides include, e.g., gentamicin, amikacin and neomycin. These compounds, however, face the possibility of clinical obsolescence because of the function of aminoglycoside-modifying enzymes, such as what already happened with kanamycins. (Wright, G. D.; Berghuis, A. M.; Mobashery, S. *Aminoglycoside antibiotics: Structures, functions and resistance*; Rosen, B. P., Mobashery, S., Eds.; Plenum Press: New York, 1998; pp. 27–69.

The tetracyclines are protein synthesis inhibitors that consist of eight related antibiotics which are all natural products of *Streptomyces*, although some can now be produced semisynthetically. Tetracycline, chlortetracycline and doxycycline are the best known. The tetracyclines are broad-spectrum antibiotics with a wide range of activity against both Gram-positive and Gram-negative bacteria. Tetracyclines have some important uses, such as in the treatment of Lyme disease.

Chloramphenicol is a protein synthesis inhibitor that has a broad spectrum of activity but it exerts a bacteriostatic effect. It is effective against intracellular parasites such as the rickettsiae. It is infrequently used in human medicine except in life-threatening situations (e.g. typhoid fever).

Macrolide antibiotics, such as erythromycin, are protein synthesis inhibitors that are active against most Gram-positive bacteria.

Some antibiotics affect the synthesis of DNA or RNA, or can bind to DNA or RNA so that their messages cannot be read. For example, nalidixic acid is a synthetic quinoloid antibiotic which is active mainly against Gram-negative bacteria. The main use of nalidixic acid is in treatment of lower urinary tract infections (UTI). In addition, the rifamycins has greater bactericidal effect against the bacteria that causes tuberculosis than other anti-tuberculosis drugs and is also useful for treatment of tuberculosis meningitis and meningitis caused by *Neisseria meningitidis*.

Growth factor analogs are structurally similar to bacterial growth factors, but do not fulfill their metabolic functions in cells. For example, sulfonamides have been extremely useful in the treatment of uncomplicated UTI caused by *E. coli*, and in the treatment of meningococcal meningitis.

The worldwide exploitation of antibiotics to treat infectious diseases has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually.

Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, the bacterium *Staphylococcus aureus* is a major cause of hospital acquired infections that, historically, responded satisfactorily to the antibiotic vancomycin. Recently, however, many strains of *S. aureus* have been found to be resistant to vancomycin. Moreover, the death rate for some communicable diseases such as tuberculosis have started to rise again, in part because of increases in bacterial resistance to antibiotics.

The development of new drugs is an essential component to strategies designed to reverse the problem of bacterial resistance, particularly in treating infectious diseases (e.g., bacterial infections). Accordingly, there is a need to identify additional compounds to treat infectious diseases (e.g., bacterial infections). The compounds can preferably be administered orally.

SUMMARY OF THE INVENTION

The present invention provides compounds (e.g., aminoglycosides) that are useful to treat or prevent infectious diseases (e.g., bacterial infections). The compounds are orally available and/or intravenously available. The compounds kill or effectively inhibit the growth of one or more Gram positive bacteria and/or one or more Gram negative bacteria. For example, the compounds of the present invention can effectively kill or effectively inhibit the growth of one or more of the following bacterium: *Escherichia coli; Pseudomonas* spp., *Proteus* spp.; *Bacteroides* spp.; *Haemophilus influenzae; Klebsiella* spp.; *Enterobacter* spp.; *Neisseria gonorrhoeae; Acinetobacter; Citrobacter* spp.; *Serratia marcescens; Branhamella* (Moraxella) *catarrhalis; Morganella morganii; Providencia stuartii; Salmonella* spp.; *Shigella* spp.; *Campilobacter* spp.; *Staphylococcus aureus; Staphylococcus epidermidis; Enterococcus faecalis; Streptococcus pyogenes; Streptococcus* (alpha-hemolytic); *Streptococcus pneumoniae*; and *Enterococcus faecium*.

The present invention provides a compound of formula (I):

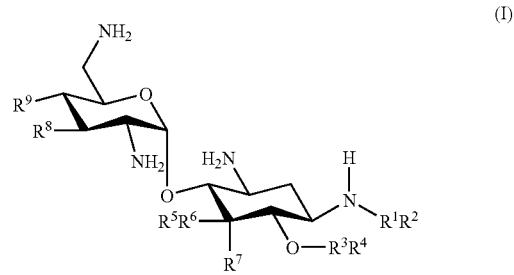

wherein:

$R^1$ is thio, sulfinyl, sulfonyl, a direct bond, or C=X, wherein X is O or S;

$R^2$ is hydrogen, $(C_1–C_{12})$alkyl, $(C_6–C_{10})$aryl $(C_1–C_{12})$alkyl, heteroaryl $(C_1–C_{12})$alkyl, or $(C_3–C_8)$cycloalkyl $(C_1–C_{12})$alkyl; wherein any alkyl, aryl, heteroaryl, or cycloalkyl is substituted with one or more amino or hydroxy;

$R^3$ is a direct bond or C=X, wherein X is O or S;

$R^4$ is $(C_1–C_{12})$alkyl optionally substituted with one or more $NR^aR^b$, wherein $R^a$ and $R^b$ are each independently hydrogen, $(C_1–C_{12})$alkyl, or $(C_6–C_{10})$aryl $(C_1–C_{12})$alkyl; wherein any alkyl or aryl of $R^4$, $R^a$ or $R^b$ is optionally substituted with one or more amino, guanidinyl, or hydroxy;

$R^5$ is hydroxy, halo, or hydrogen and $R^6$ is a direct bond; or $R^5$ is $(C_1–C_{12})$alkyl optionally substituted with one or more $NR^cR^d$, wherein $R^c$ and $R^d$ are each independently hydrogen, $(C_1–C_{12})$alkyl, or $(C_6–C_{10})$aryl $(C_1–C_{12})$alkyl, wherein any alkyl or aryl of $R^5$, $R^c$ or $R^d$ is optionally substituted with one or more amino, guanidinyl, or hydroxy; and $R^6$ is oxy, thio, or C=X, wherein X is O or S;

$R^7$ is hydrogen, halo, or hydroxy;

$R^8$ is hydrogen or hydroxy; and $R^9$ is hydrogen or hydroxy;

wherein any alkyl is optionally interrupted with one or more (e.g., 1, 2, 3, or 4) oxy, thio, sulfinyl, or sulfonyl; and wherein any alkyl, aryl, heteroaryl, or cycloalkyl is optionally substituted on carbon with one or more (e.g., 1, 2, 3, or 4) halo, cyano, nitro, trifluoromethyl, hydroxy, $(C_1–C_6)$ alkoxy, mercapto, oxo, thioxo, or $NR^eR^f$, wherein $R^e$ and $R^f$ are each independently hydrogen, $(C_1–C_{12})$alkyl, or $(C_6–C_{10})$aryl $(C_1–C_{12})$alkyl;

or a pharmaceutically acceptable salt thereof.

The present invention also provides a pharmaceutical composition. The pharmaceutical composition comprises a compound of formula (I) and a diluent or carrier. The pharmaceutical composition can optionally comprise one or more additional antibiotic agents.

The present invention also provides a method of preventing or treating a bacterial infection in a mammal (e.g., human). The method comprises administering to the mammal an effective amount of a compound of the present invention. The method can optionally comprise administering to the mammal one or more additional antibiotic agents.

The present invention also provides a method of preventing or treating a bacterial infection in a mammal (e.g., human). The method comprises administering to the mammal an effective amount of a pharmaceutical composition of the present invention. The method can optionally comprise administering to the mammal one or more additional antibiotic agents.

The present invention also provides a compound of formula (I) for use in medical therapy.

The present invention also provides the use of a compound of formula (I) for the manufacture of a medicament for treating or preventing a bacterial infection in a mammal (e.g., human).

The present invention also provides intermediates and methods of making (e.g., synthetically preparing) compounds of formula (I).

BRIEF DESCRIPTION OF THE FIGURES

FIG. 1 illustrates representative compounds of the present invention.

FIG. 2 illustrates representative compounds of the present invention.

FIG. 8 illustrates the minimum inhibitory concentrations (MIC) of representative compounds of the present invention and several known antibiotic agents against various bacterial strains.

FIG. 9 illustrates kinetic paramaters for turnover of representative compounds of the present invention and several known antibiotic agents by various enzymes.

DETAILED DESCRIPTION OF THE INVENTION

Figure 3:
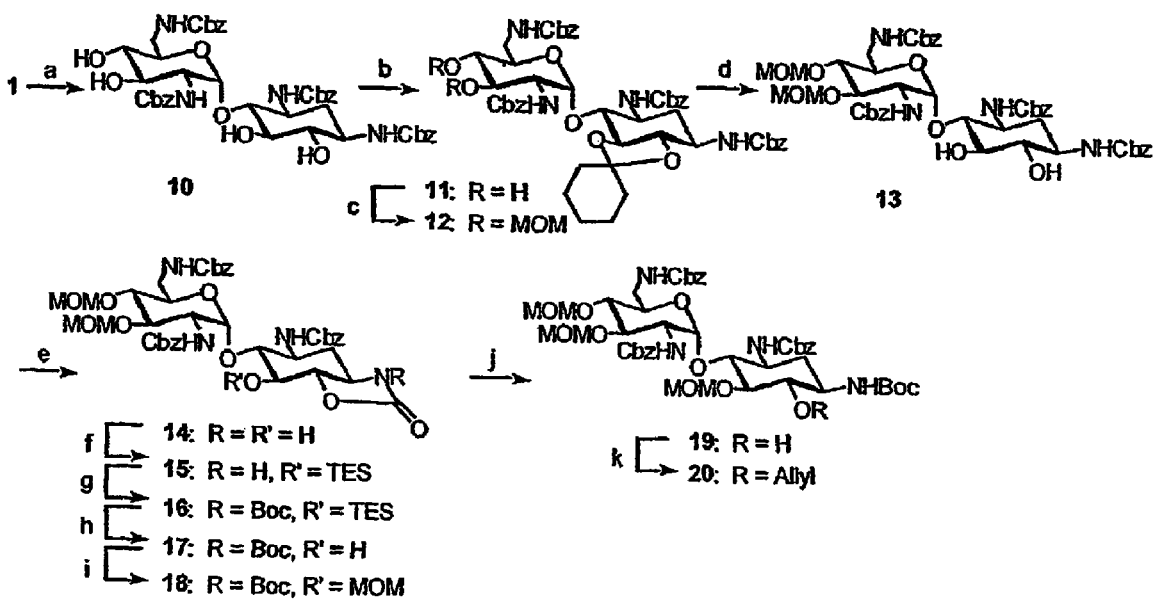
FIG. 3 illustrates a synthesis for representative compounds of the present invention.

Applicant has discovered certain compounds (e.g., aminoglycosides) that are useful to treat or prevent infectious diseases (e.g., bacterial infections). The compounds are orally available and/or intravenously available.

The following definitions are used, unless otherwise described: halo is fluoro, chloro, bromo, or iodo. Alkyl, alkylene, etc. denote both straight and branched groups; but reference to an individual group such as "propyl" embraces only the straight chain group, a branched chain isomer such as "isopropyl" being specifically referred to. Aryl denotes a phenyl group or an ortho-fused bicyclic carbocyclic group having about nine to ten ring atoms in which at least one ring is aromatic. Heteroaryl encompasses a group attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1–C_4)$alkyl, phenyl or benzyl, as well as a group of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antibacterial or antibiotic activity using the standard tests described herein, or using other similar tests which are well known in the art.

Specific and preferred values listed below for groups, substituents, and ranges, are for illustration only; they do not exclude other defined values or other values within defined ranges for the groups and substituents.

Specifically, $(C_1–C_8)$alkyl can be methyl, ethyl, propyl, isopropyl, butyl, iso-butyl, sec-butyl, pentyl, 3-pentyl, hexyl, heptyl, or octyl; $(C_1–C_6)$alkylene can be methylene, ethylene, propylene, butylene, pentylene, or hexylene; $(C_3–C_6)$cycloalkyl can be cyclopropyl, cyclobutyl, cyclopentyl, or cyclohexyl; and aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is sulfonyl, a direct bond, or C=X, wherein X is O or S.

A specific value for $R^2$ is hydrogen, $(C_1–C_{12})$alkyl, or $(C_6–C_{10})$aryl $(C_1–C_{12})$alkyl, wherein any alkyl or aryl is substituted with one or more amino and wherein any alkyl is optionally substituted with one or more hydroxy or mercapto.

Another specific value for $R^2$ is hydrogen, $(C_1–C_{12})$alkyl, or $(C_6–C_{10})$aryl $(C_1–C_{12})$alkyl, wherein any alkyl or aryl is substituted with one or more amino and wherein any alkyl is optionally substituted with one or more hydroxy or mercapto; wherein the $(C_1–C_8)$alkyl is terminally substituted with an amino or the aryl of $(C_6–C_{10})$aryl $(C_1–C_{12})$ alkyl is substituted with an amino.

A specific value for $R^1R^2$ is hydrogen or a group of the formula:

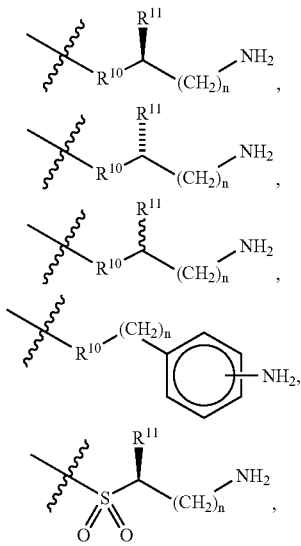

-continued

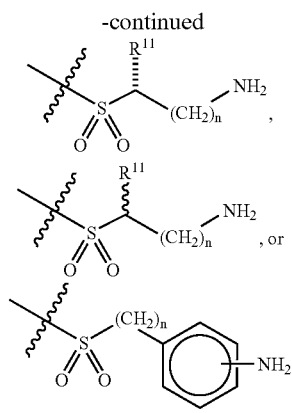

wherein
n is 0 to about 6;

$R^{10}$ is sulfinyl, sulfonyl, a direct bond, or C=X wherein X is O or S; and $R^{11}$ is hydroxy, mercapto, or $NR^gR^h$, wherein $R^g$ and $R^h$ are each independently hydrogen, $(C_1-C_8)$alkyl, or $(C_6-C_{10})$aryl $(C_1-C_8)$alkyl.

A specific value for $R^3$ is a direct bond. Another specific value for $R^3$ is C=X, wherein X is S or O.

A specific value for $R^4$ is $(C_1-C_{12})$alkyl substituted with one or more $NR^aR^b$, wherein $R^a$ and $R^b$ are each independently hydrogen, $(C_1-C_{12})$alkyl, or $(C_6-C_{10})$aryl $(C_1-C_{12})$alkyl; wherein any alkyl is optionally substituted with one or more hydroxy or mercapto.

Another specific value for $R^4$ is $(C_1-C_{12})$alkyl substituted with one or more $NR^aR^b$, wherein $R^a$ and $R^b$ are each independently hydrogen, $(C_1-C_{12})$alkyl, or $(C_6-C_{10})$aryl $(C_1-C_{12})$alkyl; wherein any alkyl or aryl of $R^4$, $R^a$ or $R^b$ is substituted with one or more amino or guanidinyl.

A specific value for $R^3R^4$ is a group of the formula:

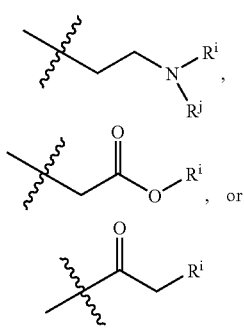

wherein
$R^i$ is hydrogen,

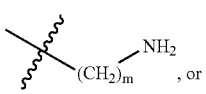

$R_j$ is

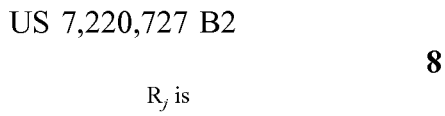

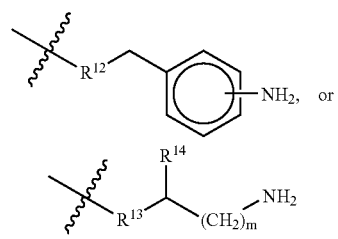

wherein $R^{12}$ is sulfinyl, sulfonyl, a direct bond, or C=X, wherein X is S or O;

$R^{13}$ is sulfinyl, sulfonyl, a direct bond, or C=X, wherein X is S or O;

$R^{14}$ is hydrogen, hydroxy, mercapto, or $NR^iR^j$, wherein $R^i$ and $R^j$ are each independently hydrogen, $(C_1-C_8)$alkyl, or $(C_6-C_{10})$aryl$(C_1-C_8)$alkyl; and m is 0 to about 8.

A specific value for $R^i$ is $(CH_2)_n-NH_2$, wherein n is 2 to about 8; or $R^i$ is guanidinyl.

A specific value for $R^j$ is hydrogen or a group of the formula:

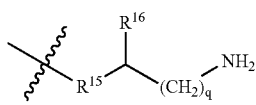

wherein $R^{15}$ is C=X, wherein X is O or S;

$R^{16}$ is hydrogen, hydroxy or amino; and q is 2.

A specific value for $R^5$ is hydroxy, halo, or hydrogen and $R^6$ is a direct bond. Another specific value for $R^5$ is $(C_1-C_{12})$alkyl optionally substituted with one or more oxo or $NR^mR^n$, wherein $R^m$ and $R^n$ are each independently hydrogen, $(C_1-C_{12})$alkyl, or $(C_6-C_{10})$aryl $(C_1-C_{12})$alkyl, wherein any alkyl or aryl of $R^5$, $R^m$ or $R^n$ is optionally substituted with one or more amino, hydroxy, or guanidinyl, and $R^6$ is oxy, thio, or C=X, wherein X is O or S.

A specific value for $R^5R^6$ is hydrogen, hydroxy, flouro, or a group of the formula:

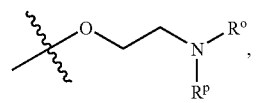

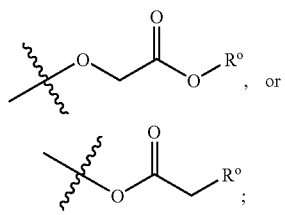

wherein
R° is hydrogen,

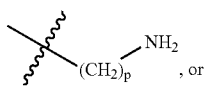, or 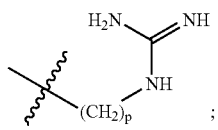 ; and

R^p is

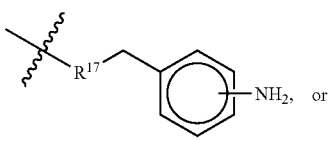

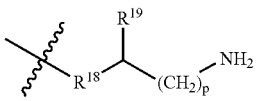

wherein
R$^{17}$ is sulfinyl, sulfonyl, a direct bond, or C=X, wherein X is S or O;
R$^{18}$ is sulfinyl, sulfonyl, a direct bond, or C=X, wherein X is S or O;
R$^{19}$ is hydrogen, hydroxy, mercapto, or NR$^q$R$^s$, wherein R$^q$ and R$^s$ are each independently hydrogen, (C$_1$–C$_8$)alkyl, or (C$_6$–C$_{10}$)aryl(C$_1$–C$_8$)alkyl; and
p is 0 to about 6.

A specific value for R$^5$R$^6$ is hydroxy.
A specific value for R$^7$ is hydrogen, fluoro, or hydroxy. Another specific value for R$^7$ is hydrogen.
A specific value for R$^8$ is hydroxy or hydrogen. Another specific value for R$^8$ is hydroxy.
A specific value for R$^9$ is hydroxy or hydrogen.
A specific value for R$^9$ is hydroxy.
A specific compound of formula (I) is

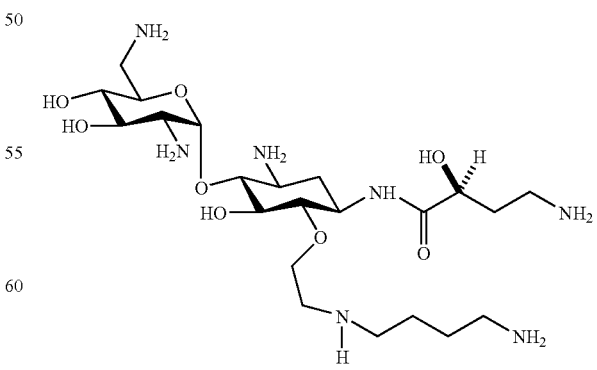

Another specific compound of formula (I) is

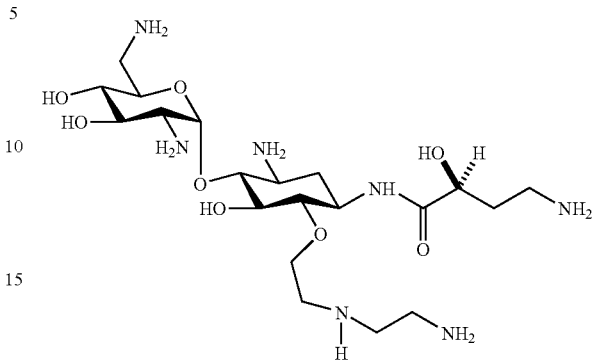

or a pharmaceutically acceptable salt thereof.

Another specific compound of formula (I) is

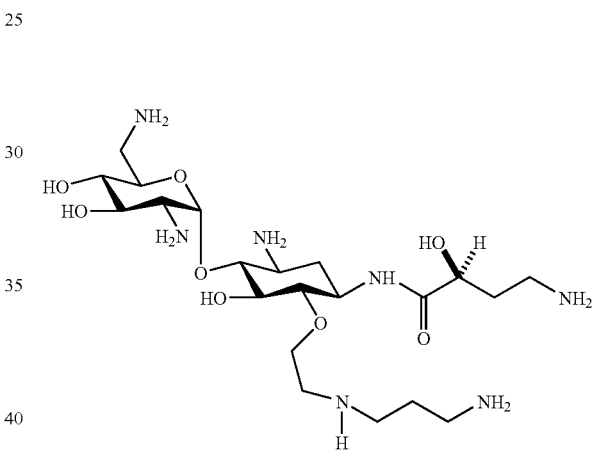

or a pharmaceutically acceptable salt thereof.

Another specific compound of formula (I) is or a pharmaceutically acceptable salt thereof.

Another specific compound of formula (I) is

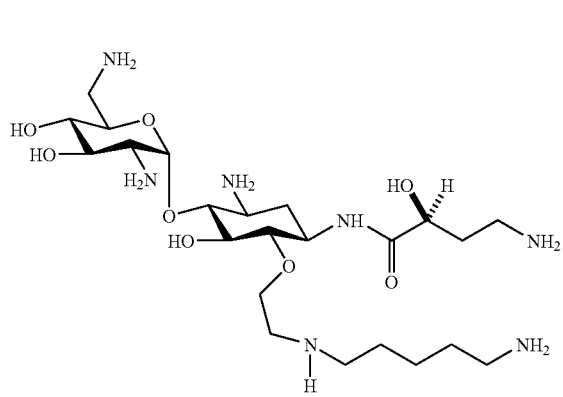

or a pharmaceutically acceptable salt thereof.

Another specific compound of formula (I) is

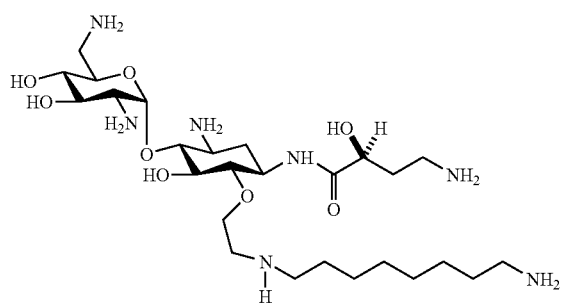

or a pharmaceutically acceptable salt thereof.

Another specific compound of formula (I) is

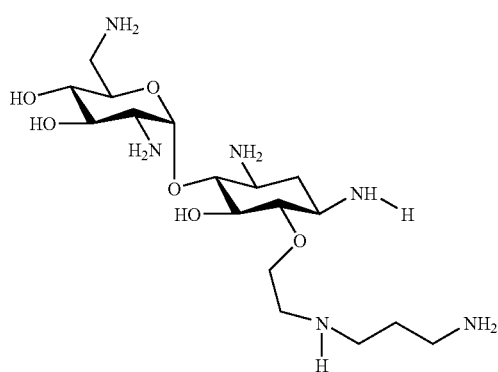

or a pharmaceutically acceptable salt thereof.

Another specific compound of formula (I) is

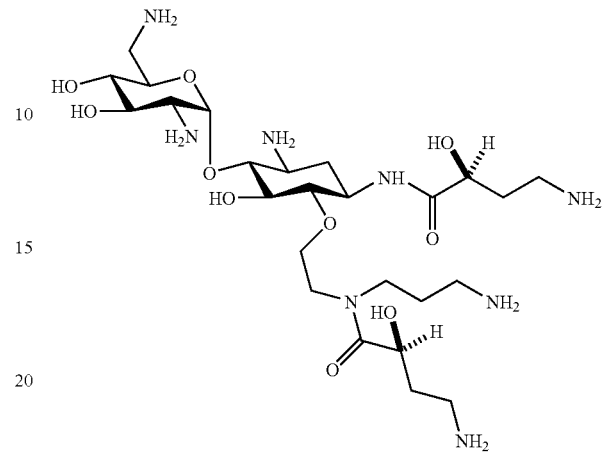

or a pharmaceutically acceptable salt thereof.

Another specific compound of formula (I) is

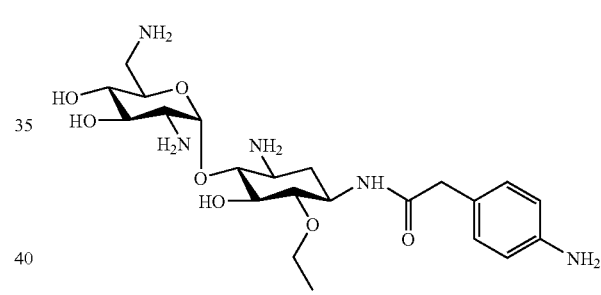

or a pharmaceutically acceptable salt thereof.

Another specific compound of formula (I) is

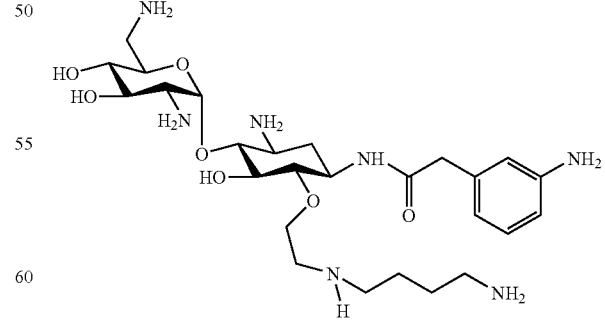

or a pharmaceutically acceptable salt thereof.

The present invention also provides intermediates as well as methods of making (e.g., synthetically preparing) compounds of the present invention (e.g., compounds of formula (I)). The compounds of the present invention can be prepared from procedures that are known to those of skill in the art or as shown herein below. Specifically, the compounds of the present invention (e.g., compounds of formula (I)) can be prepared from convenient starting materials, employing procedures (e.g., reagents and reaction conditions) known to those of skill in the art. For example, suitable reagents and reaction conditions are disclosed, e.g., in *Advanced Organic Chemistry, Part B: Reactions and Synthesis*, Second Edition, Carey and Sundberg (1983); *Advanced Organic Chemistry Reactions, Mechanisms, and Structure*, Second Edition, March (1977); Greene, T. W., *Protecting Groups In Organic Synthesis*, Third Edition, 1999, New York, John Wiley & sons, Inc.; and *Comprehensive Organic Transformations*, Second Edition, Larock (1999). Additionally, specific exemplary procedures are shown in the examples herein below.

Referring to FIG. 3, neamine hydrochloride 1 was prepared from methanolysis of the commercially available neomycin sulfate, as reported in Dutcher, J.; Donin, M. *J. Am. Chem. Soc.* 1952, 74, 3420–3422; Ford, J. H.; Bergy, M. E.; Brooks, A. A.; Garrett, E. R.; Alberti, J.; Dryer, J. R.; Carter, H. E. *J. Am. Chem. Soc.* 1955, 77, 5311–5314; Grapsas, I.; Cho, Y. I.; Mobahsery, S. *J. Org. Chem.* 1994, 59, 1918–1922. Treatment of this compound with benzylchloroformate in the presence of sodium carbonate afforded the tetra-N-Cbz protected neamine derivative 10. Kumar, V.; Remers, W. A. *J. Org. Chem.* 1978, 43, 3327–3337. This compound was subjected to 1,1-dimethoxycyclohexane to provide the mono-cyclohexylidene-protected compound 11, along with some 5,6:3',4'-di-cyclohexylidene-protected derivative, which was fully converted to 11 in the presence of p-toluenesulfonic acid and methanol in DMF. Tohma, S.; Yoneta, T.; Fukatsu, S. *J. Antibiot.* 1980, 33, 671–673.

Protection of the hydroxyl groups at positions 3' and 4' was achieved by treatment of compound 11 with chloromethyl methyl ether in the presence of Hünig's base and tetrabutylammonium iodide to give 12 in good yield. Cyclohexylidene deprotection of this compound with acetic acid afforded intermediate 13, which was treated with sodium hydride in DMF to furnish the cyclic carbamate 14 in high yield. Protection of the hydroxyl group at position 5 of 14 with triethylsilyl chloride gave the TES-protected derivative 15 (FIG. 3).

Treatment of 15 with di-tert-butyldicarbonate in the presence of triethylamine and DMAP afforded compound 16 in high yield. Attempt at the opening of the oxazolidinone ring under mild basic condition (0.5 N aqueous LiOH) gave an isomeric mixture of products having the TES group either at position 5 or 6 (due to TES migration from position 5 to 6 in the ring-opened product). Several attempts to protect the C5 hydroxyl group with a variety of different types of protective groups, prior to N-Boc protection of the cyclic carbamate, failed to give any acceptable result. For instance, attempt at MOM protection resulted in formation of a compound having the MOM groups both at the C5 oxygen and the N1 of the cyclic carbamate. Therefore, the TES group of 16 was removed by TBAF to give 17, which was treated with chloromethyl methyl ether to afford the derivative 18 in good yield.

Referring to FIG. 3, treatment of compound 18 with 0.5 N aqueous lithium hydroxide afforded the advanced intermediate 19, having the C6 hydroxyl group free for further manipulation. Compound 19 was allowed to undergo reaction with allyl bromide in the presence of lithium bis(trimethylsilyl)amide and tetrabutylammonium iodide to give the allyl protected derivative 20, according to the procedure of Park et al. Park, W. K. C.; Auer, M.; Jaksche, H., Wong, C.-H. *J. Am. Chem. Soc.* 1996, 118, 10150–10155.

Figure 4:
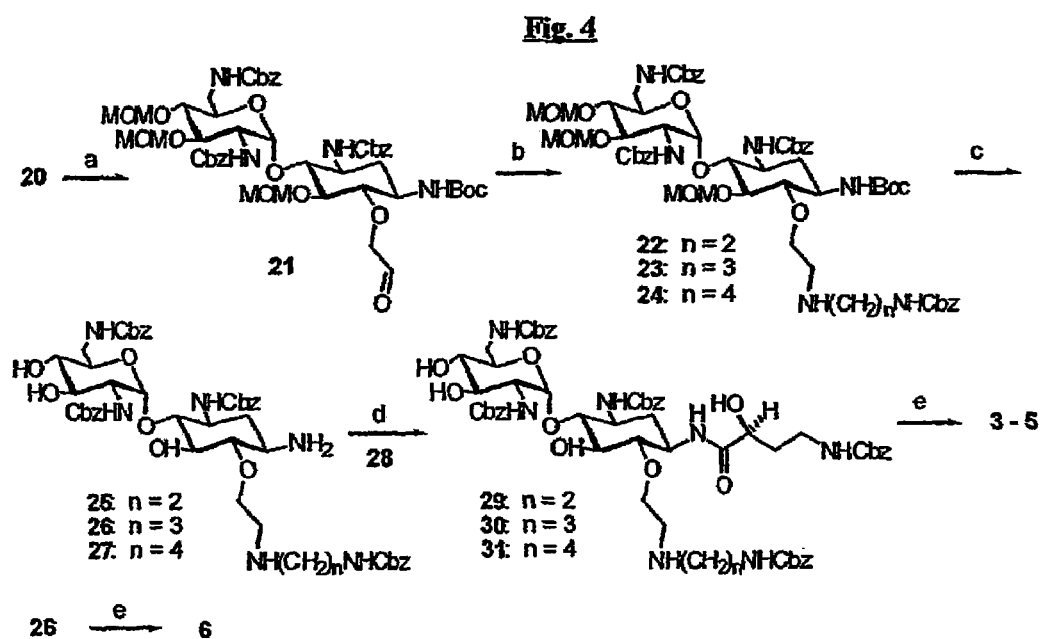
FIG. 4 illustrates a synthesis for representative compounds of the present invention.
Figure 5:
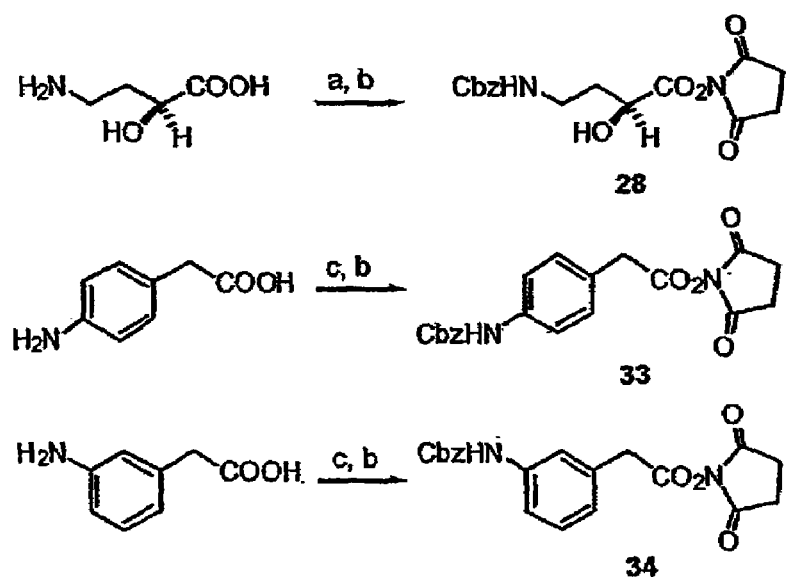
FIG. 5 illustrates a synthesis of reagents useful for praparing representative compounds of the present invention.

Referring to FIG. 4, ozonolysis of 20, followed by reductive amination of the aldehyde 21 with the corresponding mono-N-Cbz-protected diaminoalkanes, afforded the aminated products 22–24, according to similar reported methodology. Park, W. K. C.; Auer, M.; Jaksche, H., Wong, C.-H. *J. Am. Chem. Soc.* 1996, 118, 10150–10155. Efficient deprotection of the Boc and MOM groups with 1.3 N methanolic HCl resulted in the formation of derivatives 25–27, having the N1 group free for the preparation of the corresponding amides.

Figure 6:
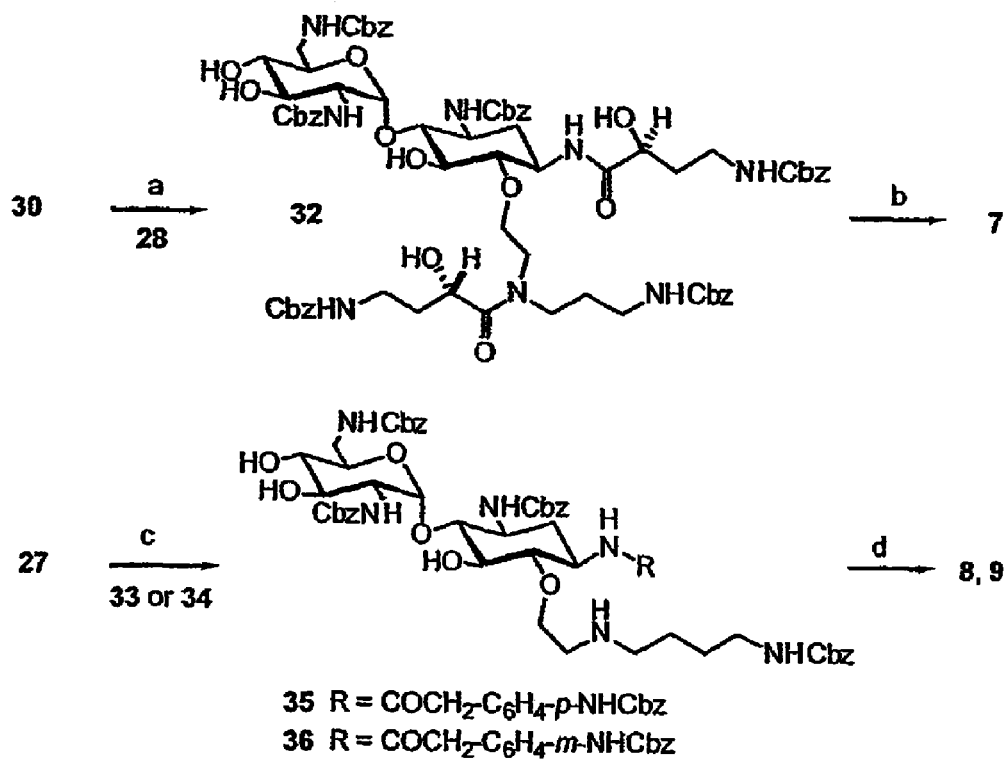
FIG. 6 illustrates a synthesis for representative compounds of the present invention.

Treatment of these compounds with activated ester of (S)-4-amino-2-hydroxybutanoic acid (FIG. 4), furnished 29–31 in good yields. Finally, removal of the Cbz groups of 29–31 and 26 by catalytic transfer hydrogenation (Felix, A. M.; Heimer, E. P.; Lambros, T. J.; Tzougraki, C.; Meienhofer, J. *J. Org. Chem.* 1978, 43, 4194–4196) with 1,4-cyclohexadiene over Pd—C afforded the title compounds 3–6 in good yields (FIG. 4). Compound 32 was prepared by treatment of 30 with 28 in pyridine, which after removal of the Cbz groups gave compound 7 (FIG. 6).

Compound 35 was prepared by treatment of 27 with 1.0 equivalent of the active ester of 4-aminophenylacetic acid (33). Deprotection of this derivative under the same condition described earlier afforded compound 8 in good yield (FIG. 6). Similarly, compound 36 was synthesized by treatment of 27 with 34, which after removal of the Cbz groups furnished 9 (FIG. 6).

One of the major difficulties in the synthesis was the preparation of the intermediate 19 from its precursor, cyclic carbamate 14 (FIG. 3). When compound 14 was treated with di-tert-butydicarbonate in the presence of Et$_3$N and DMAP, the product of the reaction was a compound with Boc groups both at C5 oxygen and N1 nitrogen. Attempts to deprotect the O-Boc group under mild basic conditions (Na$_2$CO$_3$ or LiOH) resulted in the opening of the oxazilidinone ring.

Another difficulty encountered in the final step of the synthesis was deprotection of the Cbz groups, which proved to be difficult under typical conditions. Hydrogenolysis of the Cbz protected compounds over Pd—C at atmospheric hydrogen pressure required long reaction times and afforded very low yield of the desired compounds. This problem was solved by the application of the catalytic transfer hydrogenation, using 1,4-cyclohexadiene in the presence of activated palladium on carbon and acetic acid as solvent. Felix, A. M.; Heimer, E. P.; Lambros, T. J.; Tzougraki, C.; Meienhofer, J. *J. Org. Chem.* 1978, 43, 4194–4196.

Processes for preparing compounds of formula (I), and intermediates thereof, are provided as further embodiments of the invention and are illustrated by the procedures in the examples herein below, wherein the meanings of the generic radicals are as given above unless otherwise qualified. Intermediates useful for preparing compounds of formula (I) are also provided as further embodiments of the invention.

Design Strategy

The three-dimensional NMR structure for paromomycin bound to the A-site rRNA template (Protein Data Bank Code: 1PBR) was the beginning for the design. The paromamine portion (6'-hydroxyl analogue of neamine) of paromomycin, as a minimal motif for RNA binding, was retained in the A-site template and the remainder of the paromomycin structure was removed. This complex was defined as the receptor template, and a DOCK (DOCK version 4.0, University of California at San Francisco. Ewing, T. J. A.;

Kuntz, I. D. *J. Comput. Chem.* 1997, 18, 1175–1189) search was performed using the Cambridge structural database (CSD) and the National Cancer Institute (NCI) 3-D database for molecules that would bind to this template. The two databases provided a sampling of 273,000 compounds for the three-dimensional search protocol. The list of selected compounds that emerged from the search was reduced according to steric and energetic criteria. A subset of these structures that was predicted to bind near the positions N1 and O6 of paromamine was kept. In addition to this set of compounds, attention was paid to the A-site rRNA-paromamine complex itself. The core moiety of paromamine was modified by an aminohydroxybutyryl group at position N1. At position O6, various amine-containing aliphatic substitutions were made by looking at the distance between O6 and the phosphate backbone of A-site of rRNA, using molecular graphics. The outcome of these protocols was compounds 3–9.

The rationale for selecting aminohydroxybutyryl group at position N1 was that amikacin 2 possesses such a substitution in its structure, and this particular substitution was known to impart resistance to modification by a number of aminoglycoside-modifying enzymes. Kotra, L. P.; Haddad, J.; Mobashery, S. *Antimicrob. Agents Chemother.* 2000 (in press); Wright, G. D.; Berghuis, A. M.; Mobashery, S. *Aminoglycoside antibiotics: Structures, functions and resistance*; Rosen, B. P., Mobashery, S., Eds.; Plenum Press: New York, 1998; pp. 27–69; Haddad, J.; Kotra, L. P.; Mobashery, S. *Aminoglycoside Antibiotics: Structures and Mechanism of Action*, In *Glycochemistry: Principles, Synthesis, and Applications*; Wang, G., Bertozzi, C., Eds.; Marcel Dekker, Inc: NY, 2000 (in press).

Neamine, the 6'-amino analog of paromamine, was used in the syntheses because of its ready availability from fragmentation of neomycin. The terminal amine-containing substitutions at position O6 on neamine were selected because of potential ion-pairing interactions between the amine and the phosphate backbone in the target rRNA region.

Computer Modeling

FIG. 8 shows the energy-minimized structure of compound 4 bound in the A-site of rRNA template. This compound occupies the pocket that is formed by A1492, similar to the case of other neamine class of compounds, and interacts with the phosphate backbone of the nucleic acid via ion-pairing and hydrogen-bonding interactions. In addition, the aminohydroxybutyryl moiety forms two hydrogen bonds and one ion-pair interaction with the rRNA template. The O6 side chain has one hydrogen bond with the nucleic acid base (G1405) and one ion-pairing interaction with the phosphate backbone. This model suggests that the side chains at O6 may be longer than the propylamine due to the presence of more functional groups and space to accommodate such side chains in this area. These homologous side chains will have similar interactions, such as ionic and hydrogen-bonding interactions as was seen in the case of compound 4, and indeed compound 5 showed comparable binding affinity to F-AS (vide infra).

Antibiotic Activities of Synthetic Aminoglycosides

Figure 7:
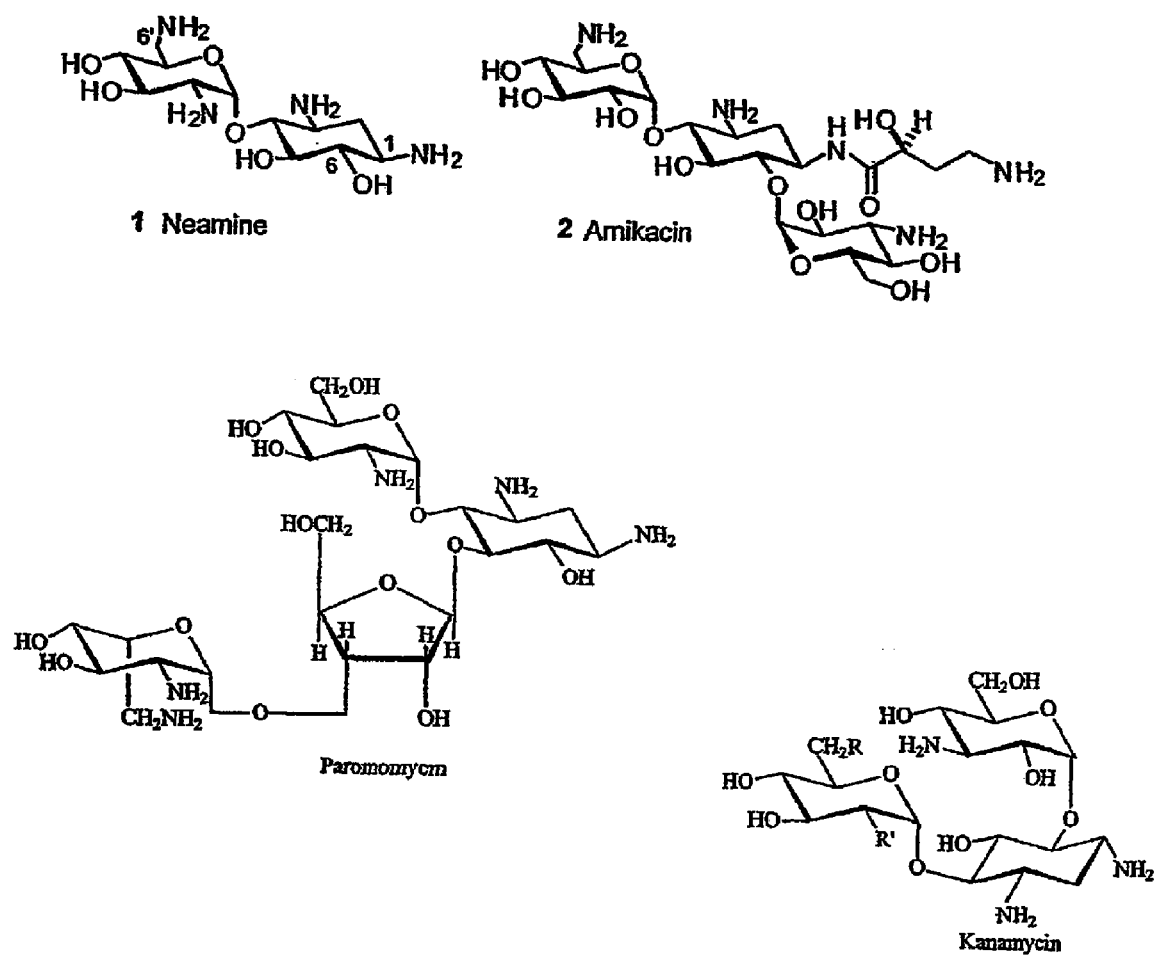
FIG. 7 illustrates several known aminoglycosides.
Figure 10:
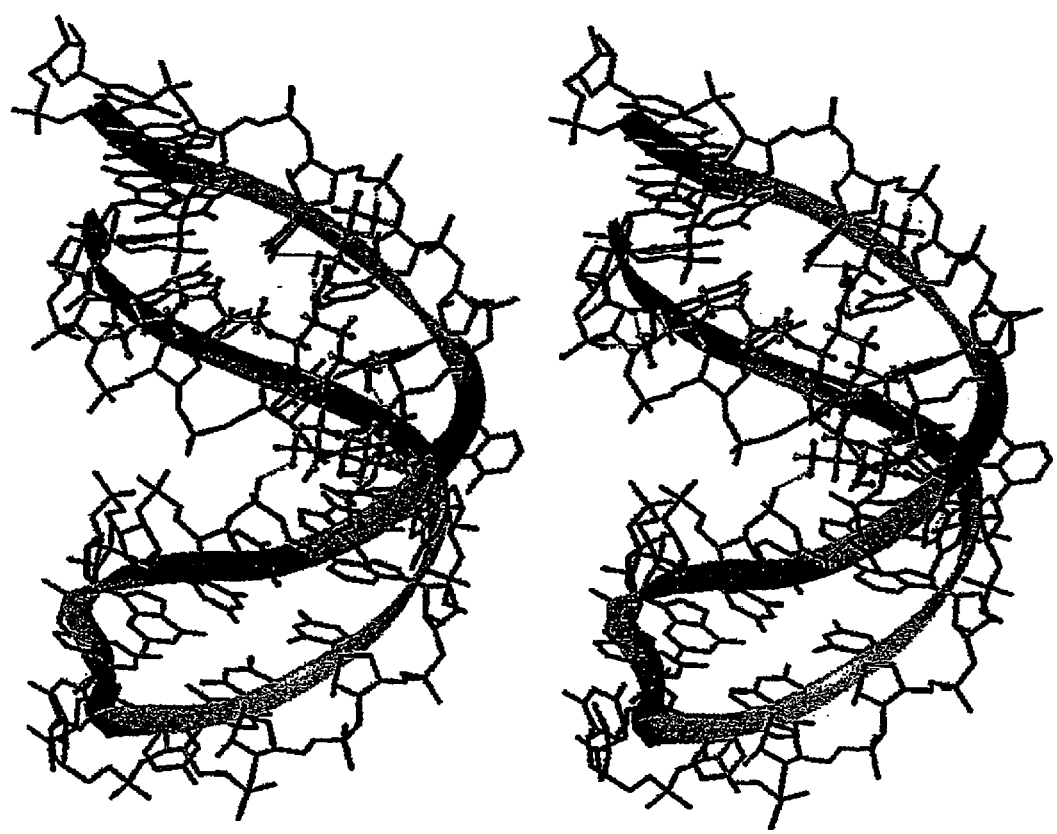
FIG. 10 illustrates a stereo view of the A-site region of the 16S ribosomal RNA template occupied by a representative compound of the present invention.

The antibiotic activities of representative compound of the present invention are shown in Table 1. For the purpose of comparison of activities and demonstration of the properties of the bacterial strains used in this study, susceptibility studies were also performed with several aminoglycosides (neamine, kanamycin A, gentamicin, tobramycin, and amikacin) and β-lactam [ampicillin (a penicillin), ceftazidime (an expanded-spectrum cephalosporin, and imipenem (a carbapenem)] antibiotics. Neamine 1 (FIG. 7) is a suitable control, since the compounds of the present invention utilize the structure of Neamine 1 as a template. Kanamycin A has become clinically obsolete, since it is an excellent substrate for the ubiquitous resistance enzymes aminoglycoside phosphotransferases (APH(3')s), and it serves as another control. Gentamicin, tobramycin and amikacin are widely used presently in clinic, either by themselves or in synergistic combinations with β-lactam antibiotics.

*Escherichia coli* JM83 is an antibiotic-sensitive laboratory strain. *E. coli* JM83 (APH(3')-I) contains high copies (500–700 copies per cell) of plasmid pUC19 with the cloned kanamycin resistance gene from transposon Tn903 that produces the type I aminoglycoside 3'-phosphotransferase. APH(3')-I is the most common aminoglycoside phosphotransferase in gram-negative bacteria. *E. coli* JM83 (AAC6'/APH2") contains a plasmid with the gene for the bifunctional aminoglycoside-modifying enzyme AAC(6')/APH (2"), which is produced by many cocci. The enzyme is able to phosphorylate at the 2" position and/or acetylate at the 6' position of various aminoglycoside antibiotics to manifest resistance for the organisms that express it. *Serratia marcescens* ATCC 13880, *Enterobacter cloacae* ATCC 3047, *Pseudomonas aeruginosa* 66 and C43 are representative important gram-negative pathogens. Aminoglycosides by themselves or in combination with other antibiotics are often used to combat these microorganisms, especially *P. aeruginosa* that is often very difficult to treat. *Staphylococcus aureus* 3 and *Enterococcus faecium* 119 are representatives of the cocci. Most of these microorganisms are intrinsically resistant to aminoglycosides (poor permeability), but in combination with β-lactam antibiotics are often used to treat infections caused by these microorganisms.

Compounds 4 and 5 show good activity against *E. coli* strain hyper-expressing either APH(3')-I or AAC(6')/APH (2") aminoglycoside-modifying enzymes (Table 1). These activities are much more superior than those of kanamycin A and neamine (250- to 1000-fold higher activities) against *E. coli* hyper-expressing APH(3')-I, and merely 8-fold lower than activities of tobramycin and amikacin. The results indicate that 4 and 5 are poorly turned over by APH(3')-I (supported by enzymology with purified enzyme; vide infra). The activity for the synthetic compounds against *E. coli* hyper-expressing AAC(6')/APH(2") is even more impressive. These compounds either have equal activity of clinical aminoglycosides, such as amikacin, or are clearly superior (8- to 250-fold) more active (as compared with kanamycin A, gentamicin, or tobramycin). Compounds 4 and 5 demonstrate excellent activities against enterobacteria, such as *S. marcescens, E. cloacae* and also *P. aeruginosa* that are sensitive or moderately resistant to aminoglycoside antibiotics, including strains also highly resistant to β-lactam antibiotics (ampicillin, ceftazidime, imipenem). In these cases, activities of compounds 4 and 5 are typically either equal or superior to those of the most active aminoglycoside(s) used in this study. Compounds 4 and 5 also show good activities against strains of *S. aureus* 3 and *E. faecium* 119 that is moderately resistant to aminoglycosides. Compound 3 (Table 1) showed the spectrum of antimicrobial activity similar to those of compounds 4 and 5 except that its MICs values were approximately four-fold higher. Compound 6 (Table 1) gave lower activity than compound 3. It is not active against *E. coli* strains producing either APH(3')-I or AAC(6')/APH(2") enzymes, although it demonstrates activity against some of the tested organisms (*E. coli* JM83, *S. marcescens* ATCC 13880, *E. cloacae*

ATCC 3047, *S. aureus* 3) that are sensitive or moderately resistant to aminoglycoside antibiotics in general. Compound 7 shows moderate activity against *E. coli* strains producing either APH(3')-I or AAC(6')/APH(2") enzymes (MICs 64 and 32 µg/mL, respectively) and also against strains of enterobacteria and *P. aeruginosa*. Finally, compounds 8 and 9 do not show any appreciable activity against any of the microorganisms tested (MICs>1000 µg/mL), despite the fact that they do bind to the RNA under the specific assay conditions used, which may indicate that these compounds may have difficulty being transported into the cytoplasm.

Kinetics of Turnover with Aminoglycoside-Modifying Enzymes

Compounds 4, 5, 8, and 9 were studied with two of the most important aminoglycoside-modifying enzymes, namely an aminoglycoside 3'-phosphotransferase (APH(3')) (Siregar, J. J.; Lerner, S. A.; Mobashery, S. *Antimicrob. Agents Chemother.* 1994, 38, 641) and the bifunctional ("BF") aminoglycoside-modifying enzyme (AAC(6')/APH (2")). Azucena, E.; Grapsas, I.; Mobashery, S. *J. Am. Chem. Soc.* 1997, 119, 2317; Daigle, D M; Hughes, D W; Wright, G D *Chem. & Biol.* 1999, 6, 99–110. The latter possesses both phosphotransferase (APH(2")) and acetyltransferase (AAC(6')) activities. These compounds are exceedingly poor substrates for these resistance enzymes under in vitro conditions (Table 2). So, in effect, they are not affected by these resistance enzymes.

The kinetic parameters for turnover of two known aminoglycosides are noted herein. Neamine is an excellent substrate for APH(3') ($k_{cat}/K_m$ of $2.9 \times 10^7$ $M^{-1}s^{-1}$), and a mid-range substrate for the acetyltransferase activity of the bifunctional enzyme ($k_{cat}/K_m$ of $4.3 \times 10^5$ $M^{-1}s^{-1}$). Despite the fact that neamine does not have the 2"-hydroxyl, it would appear that it accepts phosphate in a reaction catalyzed by the bifunctional enzyme ($k_{cat}/K_m$ of 189 $M^{-1}s^{-1}$), but the process is so inefficient that it is irrelevant for manifestation of resistance.

On the other hand, the semisynthetic amikacin was prepared for its poor interactions with many resistance enzymes. King, J. W.; White, M. C.; Todd, J. R.; Conrad, S. A. *Clin. Infect. Dis.* 1992, 14, 908–915; Kucers, A.; Bennett, N. Mc K. *The use of antibiotics*; Kucers, A., Bennett, N. McK., eds.; William Heinemann Medical Books: London, U.K. 1987; Schmitz, F. J.; Verhoef, J.; Fluit, A. C. *Eur. J. Clin. Microbiol. Infect. Dis.* 1999, 18, 414–421; Doern, G. V.; Jones, R. N.; Pfaller, M. A.; Kugler, K. C.; Beach, M. L. *Diagn. Microbiol. Infect. Dis.* 1999, 34, 65–72.

Amikacin is certainly turned over by these enzymes, but the kinetics of turnover are sufficiently inefficient that the antibiotic is viable against organisms that harbor these enzymes, with a few exceptions. For example, amikacin was made initially to counter the effect of the ubiquitous APH (3')s. As shown in Table 2, amikacin is turned over by APH(3')-II with $k_{cat}/K_m$ of $3.8 \times 10^4$ $M^{-1}s^{-1}$. Similarly, a $k_{cat}/K_m$ of $8.6 \times 10^3$ $M^{-1}s^{-1}$ and $3.5 \times 10^5$ $M^{-1}s^{-1}$ are measured for the AAC(6') and APH(2") activities, respectively, of the bifunctional enzyme for amikacin.

Compounds 4, 5, 8, and 9 are turned over by these enzymes at or below $10^4$ $M^{-1}s^{-1}$. At best, they are turned over by APH(3')-II with $k_{cat}/K_m$ of $10^4$ $M^{-1}s^{-1}$. The $K_m$ for these substrates is substantially elevated above that for the substrate neamine (i.e., 1 µM), so enzymic catalysis would not reach saturation until a substantially higher concentration of the antibiotic is reached within the bacterial cytoplasm. The same is true for both activities of the bifunctional enzyme with 4, 5, 8, and 9. The $K_m$ values for these activities were consistently above 100 µM, often substantially so, such that within the organism these concentrations cannot be reached for effective turnover of these antibiotics by the resistance enzymes. Therefore, it is observed that these antibiotics are not affected by the resistance enzymes in any significant manner, consistent with the findings of the biological activity disclosed above.

Additional Antibiotic Agents

The compound of the present invention can be co-administered with one or more additional antibiotic agents. As used herein, an "antibiotic agent" is any compound having activity against either Gram-positive or Gram-negative organisms (i.e., inhibits the growth or destroys the development of either Gram-positive or Gram-negative organisms). *Stedman's Medical Dictionary, Illustrated*, (25th Ed.), Williams & Wilkins: Baltimore (1990) and *Mosby's Medical, Nursing, & Allied Health Dictionary*, (5th Ed.), Mosby: St. Louis (1998).

Suitable antibiotic agents are disclosed, e.g., in *Physician's Desk Reference* (PDR), Medical Economics Company (Montvale, N.J.), (53rd Ed.), 1999; *Merck Index*, An Encyclopedia of Chemicals, Drugs, and *Biologicals*, (11th Ed.), Merck & Co., Inc. (Rahway, N.J.), 1989; and references cited therein.

Suitable antibiotics include, e.g., aminoglycosides, β-lactam antibiotics, cephalosporins, macrolides, miscellaneous antibiotics, penicillins, *tetracyclines*, antifungals, antimalarial agents, antituberculosis agents, antivirals, leprostatics, miscellaneous anti-infectives, quinolones, sulfonamides, urinary anti-infectives, nasal antibiotics, opthalmic antibiotics, opthalmic antivirals, opthalmic quinalones, opthalmic sulfonamides, skin and mucous membrane antibiotics, skin and mucous membrane antifungals, skin and mucous membrane antivirals, skin and mucous membrane miscellaneous anti-infectives, skin and mucous membrane scabicides and pedulicides, skin and mucous membrane antinepolasts, nitrofurans, and oxazolidinones. *Physician's Desk Reference* (PDR), Medical Economics Company (Montvale, N.J.), (53rd Ed.), 1999.

The additional antibiotic agent can effectively kill or effectively inhibit the growth of bacteria (e.g., Gram positive bacteria and/or Gram negative bacteria). For example, the additional antibiotic agent can effectively kill or effectively inhibit the growth of one or more of the following bacterium: *Escherichia coli; Pseudomonas* spp.; *Proteus* spp.; *Bacteroides* spp.; *Haemophilus influenzae; Klebsiella* spp.; *Enterobacter* spp.; *Neisseria gonorrhoeae; Acinetobacter; Citrobacter* spp.; *Serratia marcescens; Branhamella* (Moraxella) *catarrhalis; Morganella morganii; Providencia stuartii; Salmonella* spp.; *Shigella* spp.; *Campilobacter* spp.; *Staphylococcus aureus; Staphylococcus epidermidis; Enterococcus faecalis; Streptococcus pyogenes; Streptococcus* (alpha-hemolytic); *Streptococcus pneumoniae*; and *Enterococcus faecium*.

It is appreciated that those skilled in the art understand that the additional antibiotic agent useful in the present invention is the biologically active compound present in any of the additional antibiotic agents disclosed above. For example, the additional antibiotic can be a β-lactam and the β-lactam can be azactam (aztreonam), which is typically available as an injectable solution. The additional antibiotic agent, however, is (z)-2-[[[(2-amino-4-thiazolyl) [[(2S,-3S)-2-methyl-4-oxo-1-sulfo-3-azetidinyl]carbamoyl]methylene] amino]oxy]-2-methyl propionic acid. *Physician's Desk Ref-*

*erence (PDR)*, Medical Economics Company (Montvale, N.J.), (53rd Ed.), pp. 820–823, 1999.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the lice may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated in the following non-limiting examples.

EXAMPLES

Experimental Section

Proton ($^1$H) and carbon ($^{13}$C) nuclear magnetic resonance spectra were recorded on either a Varian 400 or a Varian unity-500 MHz spectrometer. Chemical shifts are recorded in parts per million (δ) relative to tetramethylsilane (δ 0.00). Infrared (IR) spectra were recorded on a Nicolet 680 DSP FTIR spectrometer. Low-resolution mass spectra (MS) were recorded on a Kratos MS 80RFA spectrometer. High-resolution mass spectra were performed by the Michigan State University Mass Spectrometry Facility. Melting points were obtained on an Electrothermal melting point apparatus and are uncorrected. Thin layer chromatography (TLC) was performed with Whatman precoated K6F silica gel 60A (0.25 mm thickness plates). The plates were visualized by either ninhydrin spray or immersion in a p-anisaldehyde solution and warming on a hot plate. All chromatography solvents were reagent grade. Tetrahydrofuran (THF) was distilled from sodium benzophenone ketyl, and dichloromethane was distilled from calcium hydride. 1,1-Dimethoxycyclohexane was purchased from the TCI America Co. N-Cbz protected diaminoalkanes were either prepared (Atwell, G. J.; Denny, W. A. *Synthesis* 1984, 1032–1033) or purchased from the Fluka chemical company as hydrochloride salt. The amine free-bases were prepared by treatment of the HCl salts with Amberlite IRA-400 (OH$^-$) ion-exchange resin. 3-Amino and 4-amino phenylacetic acids were purchased from Fluka chemical company and converted to the N-Cbz protected derivatives prior to use. Pyruvate kinase (PK), lactic dehydrogenase (LD), phospho (enol)pyruvate (PEP), ATP and NADH were purchased from the Sigma Chemical Co. All other reagents were purchased from the Aldrich Chemical Co. Spectrophotometric studies were performed on a Hewlett-Packard 8453 diode array instrument. All calculations were performed by the MS Excel program.

Determination of Minimum Inhibitory Concentration (MICs)

The MICs of all antibiotics, including the compounds of the present invention (i.e., the compounds of formula (I)), were determined by microdilution method broth procedure. Sequential twofold dilutions of antibiotics were performed in 100 µL of Luria-Bertani (LB) broth in sterile 96-well microtiter plates. Overnight cultures of bacteria were diluted 100 times in LB broth and subgrown for several hours and 10 µL of diluted cultures were transferred into the antibiotic containing microtiter plates to bring final inoculums to $10^5$ CFU/mL (CFU stands for the colony forming units). Cultures were incubated overnight at 35° C. and microtiter plates were checked from below with a reflective viewer. MICs were defined as the lowest concentrations of the drug at which the microorganism did not demonstrate visible growth.

Kinetic Determinations with Resistance Enzymes

Kinetic studies were performed for phosphotransferase activities of the bifunctional enzyme AAC(6')/APH(2") and APH(3')-IIa, as well as the acetyltransferase activity of AAC(6')/APH(2") using the methods described by Azucena et al. (Azucena, E.; Grapsas, I.; Mobashery, S. *J. Am. Chem. Soc.* 1997, 119, 2317.) The assay mixture consisted of 66 mM PIPES, pH 7.5, 11 mM magnesium acetate, 22 mM potassium acetate, 1.76 mM phosphoenol pyruvate, 0.1 mM NADH, 6.1 units of pyruvate kinase, 21 units of lactate dehydrogenase, 100 nM enzyme, the aminoglycoside substrate (at various concentrations), and 150 µM ATP in 500 µL total volume. The components of the assay mixture were mixed in a cuvette in the absence of ATP and enzyme. The solution was allowed to equilibrate at room temperature for 2 minutes. The reaction was started by the addition of ATP and enzyme. The progress of the reaction was monitored spectrophotometrically at 340 nm. Lineweaver-Burk plots were obtained to determine the $K_m$ and $k_{cat}$ values.

For the acetyltransferase activity assay, the method of Haas and Dowding was employed. (Haas, M.; Dowding, J. E. *Methods Enzymol.* 1972, 72, 248.) The reaction mixture was composed of 58 mM citric acid, 124 mM tripotassium citrate, 18 mM magnesium acetate, 6 mM dithiothreitol, the aminoglycoside substrate (at various concentrations), and 120 µM acetylcoenzyme A (specific activity, 21 mCi/mmol)

in a total volume of 30 μL. The reaction was started by the addition of 5 μL of enzyme (final concentration of 100 nM) and was stopped at 1, 2, 3, and 4 min by the addition of 10% tricholoroacetic acid. Kinetic constants were determined from Lineweaver-Burk plots.

Docking and Molecular Modeling

The NMR structure of paromomycin bound to the rRNA A-site was used as the starting template. Fourmy, D.; Recht, M. I.; Blanchard, S. C.; Puglisi, J. D. *Science* 1996, 274, 1367–1371. Rings I and II (2-deoxystreptamine and 2'-deoxy-2'-aminoglucose, respectively) in the NMR structure of paromomycin were retained and the remainder of the structure was removed. These two rings constitute the aminoglycoside paromamine (a structurally similar compound to neamine having a hydroxyl group in place of the amine at position 6'). With this structure at hand, the Connolly surface of the complex (i.e., A-site RNA template bound by paromamine) was computed, which defines the "receptor site". Two ligand databases, the NCI-3D database and Cambridge Structural Database, collectively containing a total of 273,000 compounds, were used to dock the individual compounds into the "receptor site" using the program DOCK version 4.0. The electrostatic and steric counterparts on the receptor site were matched with the docked compounds. This data set was reduced to 40 compounds based on their best fit into the "receptor site". Each compound in the set of 40 compounds was considered in the receptor site individually. These 40 compounds fit in the space near the aminoglycoside-binding site, and were scored by the program favorably for their ability to bind to the depressions and niches of the surface of the rRNA structure. Then, neamine analogues that would be covalently tethered to these entities individually were envisioned. Many of these compounds were predicted to bind the surface such that they were amenable for attachment to neamine at position N1 and O6 (marked in the structure 1). The tethers were designed such that they themselves would have potential favorable electrostatic interactions with the rRNA A-site. The visualization and structure editing were performed using Sybyl molecular modeling program. (Sybyl version 6.5, Tripos Inc., St. Louis, Mo.) This complex was energy-minimized using Amber 5.0 package. Case, D. A.; Pearlman, D. A.; Caldwell, J. W.; Cheatham III, T. E.; Ross, W. S.; Simmerling, C. L.; Darden, T. A.; Merz, K. M.; Stanton, R. V.; Cheng, A. L.; Vincent, J. J.; Crowley, M.; Ferguson, D. M.; Radmer, R. J.; Seibel, G. L.; Singh, U. C.; Weiner, P. K.; Kollman, P. A. AMBER 5. 1997, University of California, San Francisco, Calif. The point charges on compound 4 were obtained from ESP charges calculated by MOPAC package (PM3 hamiltonian) and the parameters for the carbohydrate rings were according to Woods et al. Woods, R. J.; Dwek, R. A.; Edge, C. J.; Fraser-Reid, B. *J. Phys. Chem.* 1995, 99, 3832–3846. Sodium ions were added to the complex to neutralize the system using xleap routine as implemented in Amber 5.0, and the complete molecular assembly was solvated with TIP3 waters at least 10 Å from the surface of the assembly. Energy minimization was carried out for 10,000 iterations with a non-bonded cutoff of 12 Å.

Referring to FIGS. 3–6, exemplary compounds of the present invention can be prepared as follows:

1,3,2',6'-Tetrakis(N-benzyloxycarbonyl)-5,6-O-cyclohexylideneneamine (11)

A solution of 10 (6.37 g, 7.43 mmol) and p-toluenesulfonic acid mono hydrate (210 mg, 1.11 mmol) in anhydrous DMF (150 mL) was concentrated to about 120 mL in vacuo to remove the residual water. To this solution was added 1,1-dimethoxycyclohexane (5.0 mL, 33.16 mmol) and the mixture was stirred overnight at room temperature under an atmosphere of argon. TLC of the mixture after 24 h showed the presence of some starting compound. Therefore, the mixture was concentrated to about 110 mL in vacuo to remove methanol and the other volatiles generated during the course of the reaction. To this mixture was added another portion of 1,1-dimethoxycyclohexane (2.00 mL, 13.26 mmol) and the mixture was allowed to stir at room temperature for 12 h. TLC of the mixture showed the product as a major spot ($R_f$ 0.37, 1:20 $CHCl_3$/MeOH) and the di-protected derivative ($R_f$ 0.77, 1:20 $CHCl_3$/MeOH) as a minor component. The reaction mixture was quenched by the addition of triethylamine (1.0 mL) and was concentrated to dryness in vacuo to give a residue, which was diluted with dichloromethane, extracted with water and then brine, dried ($Na_2SO_4$), and concentrated to give a solid as the crude product. The solid was purified on a column ($SiO_2$, 50:1 $CHCl_3$/MeOH) to afford 11 (3.95 g, 56.6%) and the 5,6:3',4'-di-O-cyclohexylidene derivative (2.49 g, 33%). This compound was fully converted to 11 by the following procedure: To a solution of the di-protected derivative (2.49 g, 2.22 mmol) in anhydrous DMF (35 mL) was added a solution of p-toluenesulfonic acid (28 mg, 0.15 mmol) in methanol (1 mL) and the mixture was kept at room temperature overnight. The reaction mixture was worked up and purified as described earlier to furnish another portion of 11 (2.10 g, 30%). Total yield (6.05 g, 86.6%), mp 115–117° C.; FTIR (film): 3390, 3353, 2935, 1703, 1693, 1530, 1278, 1056 $cm^{-1}$; $^1H$ NMR (500 MHz, aceton-$d_6$) δ 7.39–7.26 (m, 20H, Ph), 6.60 (d, J=7.0 Hz, 1H, NH), 6.49 (d, J=9.5 Hz, 1H, NH), 6.34 (s, 1H, NH), 6.17 (s, 1H, NH), 5.28 (s, 1H, H1'), 5.11 (d, J=12.5 Hz, 1H, C$\underline{H}_2$Ph), 5.10 (d, J=12.0 Hz, 2H, C$\underline{H}_2$Ph), 5.06 (m, 5H, C$\underline{H}_2$Ph), 3.93 (t, J=8.5, 10.0 Hz, 1H), 3.86 (m, 2H), 3.81 (m, 1H), 3.73 (m, 2H), 3.69 (t, J=10.0, 9.5 Hz, 1H), 3.52 (t, J=10.0, 9.0 Hz, 1H), 3.49 (m, 1H), 3.53 (m, 1H), 3.44 (m, 1H), 3.38 (m, 1H), 2.19 (m, 1H, H2$_{eq}$), 1.56 (m, 9H), 1.29 (m, 2H); $^{13}C$ NMR (125 MHz, aceton-$d_6$) δ 157.57, 156.68, 156.21, 155.85, 137.59 (4C), 128.55, 128.19, 128.07, 127.90, 111.82, 97.46, 80.91, 78.36, 77.60, 72.28, 71.69, 71.21, 66.19, 66.19, 66.07, 65.89, 56.08, 141.65, 49.28, 42.13, 36.40, 36.22, 24.99, 23.75; MS (FAB, NBA) calcd for $C_{50}H_{58}O_{14}N_4Na$ (M+Na$^+$) 961. found 961. (M+H$^+$) 939. found 939.

1,3,2',6'-Tetrakis(N-benzyloxycarbonyl)-5,6-O-cyclohexyl-3',4'-di-O-methoxymethylneamine (12)

To an ice-cold solution of 11 (1.74 g, 1.86 mmol), tetra-butylammonium iodide (2.73 g, 7.42 mmol), and N,N-di-isopropylethylamine (12.9 mL, 74.20 mmol) in anhydrous DMF (26 mL) was added chloromethyl methyl ether (4.22 mL, 55.65 mmol) and the mixture was stirred at 32° C. under an atmosphere of argon for 40 hrs. The reaction mixture was stirred and quenched with a saturated solution of sodium bicarbonate (5 mL) for 30 min and was concentrated to a syrup in vacuo. The resultant residue was diluted with dichloromethane and extracted with water and then brine. The organic layer was dried over magnesium sulfate, and concentrated in vacuo to give a syrup, which was purified on a column ($SiO_2$, 50:1 $CHCl_3$/MeOH) to afford 12 (1.50 g, 79%) as a white solid. mp 65–66° C.; FTIR (film): 3389, 3325, 2938, 1722, 1712, 1517, 1217, 1028 $cm^{-1}$; $^1H$ NMR (500 MHz, aceton-$d_6$) δ 7.39–7.29 (m, 20H, Ph), 6.63 (s, 1H, NH), 6.54 (d, J=8.5 Hz, 1H, NH), 6.25 (s, 1H, NH), 6.11 (d, J=8.5 Hz, 1H, NH), 5.30 (s, 1H, H1'), 5.16 (d, J=12.0 Hz, 1H, CH$_2$Ph), 5.12 (d, J=11.0 Hz, 1H, CH$_2$Ph), 5.07 (m, 5H, CH$_2$Ph), 5.01 (d, J=12.0 Hz, 1H, CH$_2$Ph), 4.86 (d, J=6.5 Hz, 1H, OCH$_2$OCH$_3$), 4.74 (d, J=6.5 Hz, 1H, OCH$_2$OCH$_3$), 4.68 (d, J=6.0 Hz, 2H, OCH$_2$OCH$_3$), 3.93 (m, 2H), 3.81 (m, 2H), 3.75 (t, J=9.0, 11.4 Hz, 1H), 3.71 (t, J=9.5, 11.5 Hz, 1H), 3.66 (m, 1H), 3.53 (m, 1H), 3.48 (t, J=9.5, 9.5 Hz, 1H), 3.34 (s, 3H, OCH$_2$OCH$_3$), 3.24 (s, 3H, OCH$_2$OCH$_3$), 2.21 (m, 1H, H2$_{eq}$), 1.55 (m, 9H), 1.33 (m, 2H); $^{13}$C NMR (125 MHz, aceton-d$_6$) δ 162.29, 156.76, 156.25, 156.25, 155.89, 137.74, 137.61, 137.141, 137.141, 128.58, 128.12, 128.00, 111.93, 98.59, 98.26, 97.24, 80.77, 79.06, 78.42, 78.33, 77.68, 69.99, 69.29, 66.18, 65.99, 65.99, 56.03, 55.46, 55.01, 141.69, 49.37, 42.04, 36.50, 36.37, 36.21, 25.07, 23.77; MS (FAB, NBA) 1049 (M+Na$^+$); HRMS (FAB, NBA) calcd for C$_{54}$H$_{67}$O$_{16}$N$_4$ (MH$^+$) 1027.4550. found 1027.4556.

1,3,2',6'-Tetrakis(N-benzyloxycarbonyl)-3',4'-di-O-methoxymethylneamine (13)

To a solution of 12 (1.50 g, 1.46 mmol) in 1:1 dioxane-water (40 mL) was added glacial acetic acid (20 mL) and the mixture was stirred at 60–65° C. for 10 hrs. The reaction mixture was concentrated to dryness in vacuo to give a residue, which was purified by column chromatography (SiO$_2$, 50:1 CHCl$_3$/MeOH) to give 13 (1.32 g, 95%) as a white solid. mp 120–122° C. FTIR (film): 3387, 3328, 2947, 1721, 1709, 1692, 1517, 1218, 1028 cm$^{-1}$. $^1$H NMR (500 MHz, pyridine-d$_5$) δ 8.34 (s, 1H, NH), 8.26 (d, J=6.4 Hz, 1H, NH), 7.98 (d, J=7.6 Hz, 1H, NH), 7.69 (s, 1H, NH), 7.34–7.14 (m, 20H, Ph), 5.97 (s, 1H, H1'), 5.46 (d, J=12.8 Hz, 1H, CH$_2$Ph), 5.35 (d, J=12.4 Hz, 1H, CH$_2$Ph), 5.27 (d, J=12.4 Hz, 1H, CH$_2$Ph), 5.22 (d, J=12.8 Hz, 1H, CH$_2$Ph), 5.20 (d, J=12.0 Hz, 1H, CH$_2$Ph), 5.17 (d, J=12.4 Hz, 1H, CH$_2$Ph), 5.14 (d, J=12.4 Hz, 1H, CH$_2$Ph), 4.99 (d, J=5.6 Hz, 1H, OCH$_2$OCH$_3$), 4.93 (d, J=11.2 Hz, 1H, CH$_2$Ph), 4.88 (d, J=6.0 Hz, 1H, OCH$_2$OCH$_3$), 4.78 (d, J=6.0 Hz, 2H, OCH$_2$OCH$_3$), 4.42 (m, 1H), 4.31 (m, 1H), 4.25 (t, J=8.8, 10.4 Hz, 1H), 4.09 (m, 1H), 3.99 (m, 2H), 3.93 (m, 1H), 3.77 (m, 3H), 3.68 (m, 1H), 3.33 (s, 3H, OCH$_2$OCH$_3$), 3.24 (s, 3H, OCH$_2$OCH$_3$), 2.42 (m, 1H, H2$_{eq}$), 1.82 (m, 1H, H2$_{ax}$); $^{13}$C NMR (125 MHz, pyridine-d$_5$) δ 157.29, 157.29, 157.10, 156.80, 138.01, 137.89, 137.89, 137.89, 128.72, 128.69, 128.66, 128.30, 128.15, 128.06, 128.01, 100.02, 98.80, 98.38, 82.55, 79.36, 78.28, 78.03, 76.57, 70.87, 66.54, 66.28, 66.23, 66.11, 56.39, 56.37, 55.85, 52.59, 141.35, 42.17, 36.00; MS (FAB, NBA) 969 (M+Na$^+$); HRMS (FAB, NBA) calcd for C$_{48}$H$_{58}$O$_{16}$N$_4$Na (M+Na$^+$) 969.3745. found 969.3778.

3,2',6'-Tris(N-benzyloxycarbonyl)-1-N,6-O-carbonyl-3',4'-di-O-methoxymethylneamine 14

To a solution of 13 (1.30 g, 1.37 mmol) in anhydrous DMF (20 mL) was added sodium hydride (220 mg, 5.50 mmol, 60% dispersion in mineral oil) and the mixture was stirred at room temperature under an atmosphere of argon for 3 h. The reaction mixture was quenched with an aqueous solution of acetic acid (5 mL, 1.0 N) and concentrated to dryness in vacuo to give a residue, which was purified on a column (SiO$_2$, 50:1 CHCl$_3$/MeOH) to furnish 14 (1.02 g, 89%) as a pure white solid. mp 94–95° C.; FTIR (film): 3380, 3332, 2940, 1764, 1720, 1710, 1528, 1251, 1216, 1018 cm$^{-1}$; $^1$H NMR (500 MHz, pyridine-d$_5$) δ 8.89 (s, 1H, NH), 8.59 (s, 1H, NH), 8.21 (d, J=9.5 Hz, 1H, NH), 8.18 (d, J=10.0 Hz, 1H, NH), 7.32–7.16 (m, 15H, Ph), 6.08 (s, 1H, H1'), 5.46 (d, J=12.5 Hz, 1H, CH$_2$Ph), 5.33 (d, J=12.5 Hz, 1H, CH$_2$Ph), 5.29 (d, J=13.0 Hz, 1H, CH$_2$Ph), 5.21 (d, J=13.0 Hz, 1H, CH$_2$Ph), 5.16 (d, J=12.0 Hz, 1H, CH$_2$Ph), 5.01 (d, J=12.5 Hz, 1H, CH$_2$Ph), 4.98 (d, J=8.5 Hz, 1H, OCH$_2$OCH$_3$), 4.87 (d, J=6.5 Hz, 1H, OCH$_2$OCH$_3$), 4.76 (d, J=6.5 Hz, 2H, OCH$_2$OCH$_3$), 4.38 (m, 1H), 4.31 (dt, J=10.0, 3.0 Hz, 1H), 4.22 (t, J=9.5, 10.5 Hz, 1H), 4.17 (m, 1H), 4.07 (t, J=8.5 Hz, 1H), 3.98 (t, J=10.5 Hz, 1H), 3.94 (m, 1H), 3.77 (t, J=9.5 Hz, 1H), 3.69 (m, 1H), 3.43 (t, J=9.5 Hz, 1H), 3.34 (s, 3H), OCH$_2$OCH$_3$), 3.20 (s, 3H, OCH$_2$OCH$_3$), 2.31 (m, 1H, H-2), 1.73 (m, 1H, H2); $^{13}$C NMR (125 MHz, pyridine-d$_5$) δ 161.14, 157.38, 157.20, 156.89, 137.88, 137.74, 137.74, 128.73, 128.73, 128.68, 128.34, 128.26, 128.11, 128.06, 99.93, 98.83, 98.35, 85.01, 83.28, 79.08, 78.23, 73.94, 70.98, 66.77, 66.38, 66.29, 56.42, 56.08, 55.81, 54.41, 52.54, 42.13, 33.61; MS (FAB, NBA) 861 (M+Na$^+$); HRMS (FAB, NBA) calcd for C$_{41}$H$_{50}$O$_{15}$N$_4$Na (M+Na$^+$) 861.3170. found 861.3170.

3,2',6'-Tris(N-benzyloxycarbonyl)-1-N,6-O-carbonyl-5-O-triethylsilyl-3',4'-di-O-methoxymethylneamine (15)

To a mixture of 14 (1.02 g, 1.22 mmol), triethylamine (0.2 mL), imidazole (372 mg, 5.70 mmol), and N,N-dimethylaminopyridine (45 mg, 0.36 mmol) in anhydrous DMF (10 mL) was added triethylsilyl chloride (0.61 mL, 3.65 mmol). The mixture was stirred at room temperature under an atmosphere of argon for 5 h and then quenched with an aqueous solution of saturated sodium bicarbonate (2 mL). The mixture was concentrated to a syrup in vacuo, diluted with dichloromethane, washed with water and then brine, dried (Na$_2$CO$_3$), and concentrated to give a residue, which was purified on a column (SiO$_2$, 50:1 CHCl$_3$/MeOH) to afford 15 (925 mg, 80%) as a white solid. mp 79–80° C.; FTIR (film): 3332, 3319, 2953, 2877, 1764, 1722, 1710, 1529, 1215 cm$^{-1}$; $^1$H NMR (500 MHz, pyridine-d$_5$) δ 8.63 (s, 1H, NH), 8.18 (d, J=10.5 Hz, 1H, NH), 8.12 (d, J=9.0 Hz, 1H, NH), 7.83 (s, 1H, NH), 7.32–7.20 (m, 15H, Ph), 6.00 (s, 1H, H1'), 5.48 (d, J=12.0 Hz, 1H, CH$_2$Ph), 5.41 (d, J=12.0 Hz, 1H, CH$_2$Ph), 5.29 (d, J=13.0 Hz, 1H, CH$_2$Ph), 5.16 (m, 3H, CH$_2$Ph), 4.98 (d, J=6.5 Hz, 1H, OCH$_2$OCH$_3$), 4.88 (d, J=6.5 Hz, 1H, OCH$_2$OCH$_3$), 4.77–4.74 (m, 2H, OCH$_2$OCH$_3$), 4.45 (m, 1H), 4.35 (td, J=11.0, 2.4 Hz, 1H), 4.21 (t, J=9.5 Hz, 1H), 4.16 (m, 1H), 4.12 (t, J=9.5 Hz, 1H), 4.02 (t, J=8.5 Hz, 1H), 3.85 (m, 1H), 3.77 (m, 2H), 3.69 (m, 1H), 3.37 (m, 1H), 3.32 (s, 3H, OCH$_2$OCH$_3$), 3.17(s, 3H, OCH$_2$OCH$_3$), 2.26 (m, 1H, H2$_{eq}$), 1.72 (m, 1H, H2$_{ax}$), 0.97 [t, J=7.5 Hz, 9H, Si(CH$_2$CH$_3$)$_3$], 0.82 [m, 6H, Si(CH$_2$CH$_3$)$_3$]; $^{13}$C NMR (125 MHz, pyridine-d$_5$) δ 160.48, 157.44, 157.08, 156.79, 137.86, 137.73, 137.50, 128.83, 128.79, 128.76, 128.73, 128.35, 128.30, 128.13, 128.05, 98.82, 98.52, 98.43, 84.01, 81.08, 79.03, 78.35, 76.44, 70.53, 66.90, 66.85, 66.23, 56.43, 55.89, 55.48, 54.23, 141.98, 42.24, 33.36, 7.29, 5.28; MS (FAB, Gly) 953 (MH$^+$); HRMS (FAB, Gly) calcd for C$_{47}$H$_{65}$O$_{15}$N$_4$Si (MH$^+$) 953.4215. found 953.4191.

3,2',6'-Tris(N-benzyloxycarbonyl)-1-N-tert-butoxylcarbonyl-1-N,6-O-carbonyl-5-O-triethylsilyl-3',4'-di-O-methoxymethylneamine (16)

To a solution of 15 (910 mg, 0.96 mmol), 4-(N,N-dimethylamino)pyridine (23 mg, 0.19 mmol), and triethylamine (0.17 mL, 1.22 mmol) in dry THF (10 mL) was added di-tert-butyldicarbonate (271 mg, 1.24 mmol). The mixture was stirred at room temperature under an atmosphere of argon for 4 h. The solution was concentrated to dryness in vacuo to give a residue, which was purified on a column (SiO$_2$, 100:1 CHCl$_3$/MeOH) to give 16 (965 mg, 96%) as a white solid. mp 76–77° C.; FTIR (film): 3342, 2953, 2878, 1812, 1726, 1515, 1327, 1157, 1021 cm$^{-1}$; $^1$H NMR (500 MHz, pyridine-d$_5$) δ 7.88 (d, J=10.0 Hz, 1H, NH), 7.85 (d, J=8.5 Hz, 1H, NH), 7.46 (m, 1H, NH), 7.13–6.74 (m, 15H, Ph), 5.60 (s, 1H, H1'), 5.08 (d, J=12.5 Hz, 1H, CH$_2$Ph), 5.04 (d, J=12.0 Hz, 2H, CH$_2$Ph), 4.93 (d, J=12.0 Hz, 1H, CH$_2$Ph), 4.82 (d, J=13.0 Hz, 1H, CH$_2$Ph), 4.79 (d, J=13.5 Hz, 1H, CH$_2$Ph), 4.71 (d, J=11.5 Hz, 1H, CH$_2$Ph), 4.60 (d, J=6.5 Hz, 1H, OCH$_2$OCH$_3$), 4.52 (d, J=6.0 Hz, 1H, OCH$_2$OCH$_3$), 4.40 (d, J=7.0 Hz, 1H, OCH$_2$OCH$_3$), 4.35 (d, J=7.0 Hz, 1H, OCH$_2$OCH$_3$), 4.10 (m, 1H), 3.98 (td, J=10.5, 3.5 Hz, 1H), 3.83 (t, J=9.5 Hz, 1H), 3.74–3.70 (m, 1H), 3.47 (m, 1H), 3.39 (t, J=9.5 Hz, 1H), 3.30 (m, 1H), 2.94 (s, 3H, OCH$_2$OCH$_3$), 2.78 (s, 3H, OCH$_2$OCH$_3$), 2.56 (m, 1H, H2$_{eq}$), 1.41 (m, 1H, H2$_{ax}$), 0.98 (m, 9H, OCO$^t$Bu), 0.58 [t, 9H, Si(CH$_2$CH$_3$)$_3$], 0.42 [m, 6H, Si(CH$_2$CH$_3$)$_3$]; $^{13}$C NMR (125 MHz, pyridine-d$_5$) δ 157.06, 156.72, 156.44, 152.23, 150.00, 137.55, 137.27, 137.11, 128.47, 128.43, 128.39, 128.37, 127.99, 127.86, 127.76, 127.69, 127.58, 98.43, 98.18, 98.04, 83.03, 80.37, 80.20, 78.59, 78.03, 75.56, 70.03, 66.58, 66.49, 65.78, 56.04, 55.97, 55.49, 55.09, 141.48, 41.86, 32.48, 27.36, 6.84, 4.88; MS (FAB, NBA) 1075 (M+Na$^+$); HRMS (FAB, NBA) calcd for C$_{52}$H$_{72}$O$_{17}$N$_4$SiNa (M+Na$^+$) 1075.4560. found 1075.4566.

3,2',6'-Tris(N-benzyloxycarbonyl)-1-N-tert-butoxyl-carbonyl-1-N,6O-carbonyl-3',4'-di-O-methoxymethylneamine (17)

To an ice-cold solution of 16 (1.01 g, 0.96 mmol) in THF (10 mL) was added a 1.0 M solution of tetrabutylammonium fluoride in THF (0.96 mL, 0.96 mmol) and the mixture was allowed to stir at this temperature for 10 min. The reaction mixture was quenched by the addition of ice water (2 mL), concentrated to a syrup in vacuo, diluted with water and extracted with dichloromethane (3×30 mL). The organic layer was washed with brine, dried over sodium sulfate, and concentrated to give a residue, which was purified on a column (SiO$_2$, 70:1 CHCl$_3$/MeOH) to afford 17 (770 mg, 85%) as a white solid. mp 82–83° C.; FTIR (film): 3350, 2952, 1812, 1724, 1521, 1254, 1018 cm$^{-1}$; $^1$H NMR (500 MHz, pyridine-d$_5$) δ 8.73 (s, 1H, NH), 8.38 (d, J=8.0 Hz, 1H, NH), 8.24 (d, J=9.0 Hz, 1H, NH), 7.45–7.25 (m, 15H, Ph), 6.19 (s, 1H, H1'), 5.55 (d, J=12.0 Hz, 1H, CH$_2$Ph), 5.44 (d, J=12.5 Hz, 1H, CH$_2$Ph), 5.40 (d, J=12.5 Hz, 1H, CH$_2$Ph), 5.29 (m, 2H, CH$_2$Ph), 5.09 (m, 2H), 5.00 (m, 1H), 4.95 (d, J=6.5 Hz, 1H, OCH$_2$OCH$_3$), 4.86 (m, 2H), 4.51 (m, 1H), 4.41 (m, 1H), 4.28 (m, 4H), 4.06 (t, J=10.5 Hz, 1H), 4.00 (m, 1H), 3.87 (t, J=9.0 Hz, 1H), 3.82 (m, 2H), 3.44 (s, 3H, OCH$_2$OCH$_3$), 3.29 (s, 3H, OCH$_2$OCH$_3$), 3.10 (m, 1H), 1.93 (m, 1H, H2$_{eq}$), 1.48 (s, 10H); $^{13}$C NMR (125 MHz, pyridine-d$_5$) δ 155.85, 155.65, 155.37, 151.71, 148.95, 136.39, 136.17, 136.17, 127.27, 127.22, 127.17, 126.76, 126.62, 126.56, 98.33, 97.30, 90.83, 81.79, 81.05, 80.15, 77.55, 76.72, 71.98, 69.32, 65.31, 64.90, 64.73, 55.07, 54.90, 54.49, 54.29, 50.91, 40.59, 31.57, 26.26; MS (FAB, NBA) 959 (M+Na$^+$); HRMS (FAB, NBA) calcd for C$_{46}$H$_{58}$O$_{17}$N$_4$Na (M+Na$^+$) 961.3694. found 961.3683.

3,2',6'-Tris(N-benzyloxycarbonyl)-1-N-tert-butoxyl-carbonyl-1-N,6-O-carbonyl-5,3',4'-tri-O-methoxymethylneamine (18)

To an ice-cold solution of 17 (661 mg, 0.70 mmol), tetra-butylammonium iodide (520 mg, 1.41 mmol), and N,N-di-isopropylethylamine (2.46 mL, 14.09 mmol) in anhydrous DMF (5.00 mL) was added chloromethyl methyl ether (0.85 mL, 10.57 mmol) dropwise. The mixture was allowed to stir at 32° C. under an atmosphere of argon for 34 h. The reaction mixture was then quenched by the addition of a saturated solution of sodium bicarbonate (0.5 mL), diluted with water, and was extracted with dichloromethane (3×10 mL). The organic layer was washed with brine, dried (Na$_2$SO$_4$), and concentrated in vacuo to give a syrup, which was purified on a column (SiO$_2$, 80:1 CHCl$_3$/MeOH) to furnish 18 (673 mg, 97%) as a white solid. mp 82–83° C.; FTIR (film): 3338, 2944, 1812, 1724, 1523, 1154, 1020 cm$^{-1}$; $^1$H NMR (500 MHz, pyridine-d$_5$) δ 8.38 (d, J=9.0 Hz, 1H, NH), 8.32 (d, J=9.5 Hz, 1H, NH), 8.08 (m, 1H, NH), 7.67–7.30 (m, 15H, Ph), 5.84 (d, J=3.0 Hz, 1H, H1'), 5.55 (d, J=12.5 Hz, 1H, CH$_2$Ph), 5.39 (d, J=13.0 Hz, 1H, CH$_2$Ph), 5.35 (m, 2H), 5.31 (d, J=13.0 Hz, 1H, CH$_2$Ph), 5.27 (d, J=12.5 Hz, 1H, CH$_2$Ph), 5.07 (d, J=6.0 Hz, 1H, OCH$_2$OCH$_3$), 5.03 (d, J=6.0 Hz, 1H, OCH$_2$OCH$_3$), 4.98 (s, 1H), 4.95 (d, J=7.0 Hz, 1H, OCH$_2$OCH$_3$), 4.84 (m, 2H), 4.49 (m, 1H), 4.40–4.36 (m, 1H), 4.25 (m, 2H), 4.17 (t, J=8.0 Hz, 1H), 4.02 (t, J=9.5 Hz, 1H), 3.98 (m, 2H), 3.87 (t, J=9.0 Hz, 1H), 3.80 (m, 2H), 3.46 (s, 3H, OCH$_2$OCH$_3$), 3.42 (s, 3H, OCH$_2$OCH$_3$), 3.29 (s, 3H, OCH$_2$OCH$_3$), 3.07 (m, 1H), 1.88 (m, 1H), 1.47 (s, 9H, OCO$^t$Bu); $^{13}$C NMR (125 MHz, pyridine-d$_5$) δ 157.01, 156.67, 156.43, 152.40, 150.03, 137.54, 137.27, 137.21, 128.42, 128.37, 128.29, 128.17, 127.94, 127.89, 127.78, 127.71, 127.63, 98.99, 98.43, 97.99, 97.09, 83.08, 79.75, 79.69, 78.98, 78.33, 77.87, 70.31, 66.54, 66.30, 65.84, 56.15, 55.81, 55.43, 55.16, 141.78, 41.67, 32.44, 27.36; MS (FAB, NBA) 983 (MH$^+$); HRMS (FAB, NBA) calcd for C$_{48}$H$_{63}$O$_{18}$N$_4$ (MH$^+$) 983.4138. found 983.4150. HRMS (FAB, NBA) calcd for C$_{48}$H$_{62}$O$_{18}$N$_4$Na (M+Na$^+$) 1005.3960. found 1005.3964.

3,2',6'-Tris(N-benzyloxycarbonyl)-1-N-tert-butoxyl-carbonyl-5,3',4'-tri-O-methoxymethylneamine (19)

To a solution of 18 (673 mg, 0.69 mmol) in dioxane (10.0 mL) was added a 0.5 N aqueous solution of lithium hydroxide (5.0 mL) and the mixture was stirred at room temperature for 30 min. The reaction mixture was quenched with 0.5 N acetic acid (5.0 mL) and concentrated in vacuo to give a syrup, which was purified by chromatography (SiO$_2$, 80:1 CHCl$_3$/MeOH) to afford 19 (574 mg, 88%) as a white solid. R$_f$ 0.25 (29:1 CHCl$_3$/MeOH); mp 147–148° C.; FTIR (film): 3343, 3331, 2945, 1719, 1699, 1528, 1254, 1017 cm$^{-1}$; $^1$H NMR (400 MHz, pyridine-d$_5$) δ 8.50 (d, J=8.4 Hz, 1H, NH), 8.09 (d, J=8.0 Hz, 1H, NH), 7.74 (m, 1H, NH), 7.43–7.22 (m, 15H, Ph), 6.31 (s, 1H, OH), 5.84 (s, 1H, H1'), 5.58 (d, J=12.8 Hz, 1H, CH$_2$Ph), 5.38 (m, 3H), 5.30 (d, J=12.0 Hz, 1H, CH$_2$Ph), 5.24 (d, J=12.4 Hz, 1H, CH$_2$Ph), 5.17 (d, J=7.6 Hz, 1H, OCH$_2$OCH$_3$), 5.09 (d, J=4.0 Hz, 1H, OCH$_2$OCH$_3$), 5.00 (m, 1H), 4.90 (d, J=6.4 Hz, 1H, OCH$_2$OCH$_3$), 4.86 (d, J=6.0 Hz, 1H, OCH$_2$OCH$_3$), 4.53 (m, 1H), 4.44–4.40 (m, 1H), 4.32 (t, J=9.2 Hz, 1H), 4.15 (m, 1H), 4.00 (m, 2H), 3.88 (m, 2H), 3.75 (m, 2H), 3.49 (t, J=9.2 Hz, 1H), 3.43 (s, 3H, OCH$_2$OCH$_3$), 3.42 (s, 3H, OCH$_2$OCH$_3$), 3.35 (s, 3H, OCH$_2$OCH$_3$), 2.47 (m, 1H, H2$_{eq}$), 1.82 (m, 1H, H2$_{ax}$), 1.48 (s, 9H, OCO$^t$Bu); $^{13}$C NMR (100 MHz, pyridine-d$_5$) δ 157.35, 157.13, 156.76, 156.141, 137.77, 137.77, 137.77, 128.78, 128.75, 128.70, 128.61, 128.47, 128.27, 128.24, 128.12, 128.05, 99.23, 99.20, 98.80, 98.43, 87.22, 79.84, 78.86, 78.26, 78.16, 75.34, 70.61, 66.67, 66.60, 66.29, 56.36, 56.06, 55.88, 55.78, 52.07, 50.89, 42.05, 35.68, 28.43; MS (FAB, NBA) 957 (MH$^+$); HRMS (FAB, NBA)

calcd for $C_{47}H_{65}O_{17}N_4$ (MH$^+$) 957.4344. found 957.4319; HRMS (FAB, NBA). calcd for $C_{47}H_{64}O_{17}N_4Na$ (M+Na$^+$) 979.4164. found 979.4140.

6-O-Allyl-3,2',6'-Tris(N-benzyloxycarbonyl)-1-N-tert-butoxylcarbonyl-5,3',4'-tri-O-methoxymethyl-neamine (20)

To a solution of 19 (890 mg, 0.930 mmol) and tetra-butylammonium iodide (420 mg, 1.136 mmol) in anhydrous DMSO (2 mL) was added lithium bis(trimethylsilyl)amide (1.16 mL, 1.0 M solution in THF). To this mixture was added allyl bromide (99 μL, 1.125 mmol) dropwise and the mixture was allowed to stir at room temperature for 1 h. The mixture was quenched by the addition of AcOH (20% aqueous solution), diluted with water and extracted with ethyl acetate (3×30 mL). The organic layer was back extracted with brine, dried (Na$_2$SO$_4$) and concentrated in vacuo to give a yellow solid as crude product. The solid was purified on a column (SiO$_2$, 100:1:0.1 CHCl$_3$/MeOH/NH$_4$OH) to furnish 20 (643 mg, 69%) as a pure white solid. R$_f$ 0.42 (29:1 CHCl$_3$/MeOH); mp 163–165° C.; FTIR (film): 3334, 2928, 1721, 1708, 1703, 1692, 1529, 1253, 1147, 1042, 1017 cm$^{-1}$; $^1$H NMR (500 MHz, pyridine-d$_5$) δ 8.28 (d, J=8.0 Hz, 1H, NH), 8.14 (d, J=7.5 Hz, 1H, NH), 7.79 (d, J=7.5 Hz, 1H, NH), 7.65 (m, 1H, NH), 7.44–7.27 (m, 15H, Ph), 6.08 (m, 1H), 5.84 (s, 1H, H1'), 5.56 (d, J=12.0 Hz, 1H, CH$_2$Ph), 5.41 (d, J=12.0 Hz, 1H, CH$_2$Ph), 5.34 (m, 3H), 5.25 (d, J=12.0 Hz, 1H, CH$_2$Ph), 5.08 (m, 3H), 4.99 (m, 3H), 4.99 (d, J=6.5 Hz, 1H, OCH$_2$OCH$_3$), 4.85 (d, J=5.5 Hz, 1H, OCH$_2$OCH$_3$), 4.53 (m, 1H), 4.40 (m, 2H), 4.32 (t, J=10.5 Hz, 1H), 4.02 (m, 2H), 3.89 (m, 2H), 3.78 (m, 1H), 3.50 (m, 1H), 3.48 (m, 1H), 3.48 (s, 3H, OCH$_2$OCH$_3$), 3.38 (s, 3H, OCH$_2$OCH$_3$), 3.38 (s, 3H, OCH$_2$OCH$_3$), 2.23 (m, 1H, H2$_{eq}$), 1.95 (m, 1H, H2$_{ax}$), 1.52 (s, 9H, OCO$^t$Bu); $^{13}$C NMR (125 MHz, pyridine-d$_5$) δ 157.03, 156.77, 156.36, 155.67, 137.49, 137.49, 137.49, 135.58, 128.39, 128.35, 128.09, 127.86, 127.76, 127.69, 115.81, 98.81, 98.80, 98.44, 98.09, 83.53, 82.69, 79.48, 78.45, 77.97, 77.84, 73.26, 70.33, 66.29, 66.21, 65.94, 56.21, 55.99, 55.53, 55.44, 50.60, 50.38, 41.77, 35.08, 28.12; MS (FAB, NBA) 997 (MH$^+$); HRMS (FAB, NBA) calcd for $C_{50}H_{69}O_{17}N_4$ (MH$^+$) 997.4658. found 997.4699. HRMS (FAB, NBA). calcd for $C_{50}H_{68}O_{17}N_4Na$ (M+Na$^+$) 1019.4480. found 1019.4529.

3,2',6'-Tris(N-benzyloxycarbonyl)-1-N-tert-butoxyl-carbonyl-5,3',4'-tri-O-methoxymethyl-6-O-(2-oxoet-hyl)neamine (21)

Ozone was bubbled into a solution of 20 (400 mg, 0.401 mmol) in dichloromethane (10 mL) at −78° C. until a light blue color persisted (~10 min). The reaction mixture was flushed with O$_2$ and quenched by the addition of triphenyl phosphine (160 mg, 0.600 mmol), followed by warming up to room temperature. The solution was stirred for 1 h prior to the removal of the solvent in vacuo. The crude product can be used for the next step without further purification. The analytical sample was prepared by purification of the solid by column chromatography (SiO$_2$, 100:1:0.1 CHCl$_3$/MeOH/NH$_4$OH) to give 21 (327 mg, 81%) as a white solid. R$_f$ 0.53 (19:1 CHCl$_3$/MeOH); mp 93–95° C.; FTIR (film): 3329, 2932, 1716, 1702, 1537, 1455, 1252, 1156, 1027 cm$^{-1}$; $^1$H NMR (400 MHz, pyridine-d$_5$) δ 9.96 (s, 1H), 8.41–8.34 (m, 2H, NH), 8.05 (d, J=8 Hz, 1H, NH), 7.78 (s, 1H, NH), 7.57–7.32 (m, 15H, Ph), 6.16 (m, 1H), 5.86 (d, J=12.0 Hz, 1H, H1'), 5.52–5.21 (m, 6H), 5.14–4.97 (m, 4H), 4.9 (d, J=6.4 Hz, 1H), 4.86 (t, J=4.8 Hz, 1H), 4.52 (s, 1H), 4.41–4.29 (m, 2H), 4.18 (s, 2H), 4.12–4.00 (m, 2H), 3.87 (s, 1H), 3.79–3.71 (m, 1H), 3.60 (s, 1H), 3.51–3.33 (m, 10 H), 2.89 (s, 1H, H2$_{eq}$), 1.87 (q, J=12.4 Hz, 1H, H2$_{ax}$), 1.48 (s, 3H), 1.44 (s, 6H); $^{13}$C NMR (100 MHz, pyridine-d$_5$) δ 199.0 (weak), 157.8, 157.5157.1, 154.6, 138.2, 138.1, 129.2, 129.1, 128.9, 128.6, 128.5, 128.4, 123.6, 99.7 (C1'), 99.2, 98.8, 82.7, 82.2, 81.7, 80.8, 80.6, 80.4, 80.2, 79.2, 78.6, 76.5, 75.7, 73.2, 72.7, 72.0, 71.0, 67.1, 67.0, 66.7, 56.8, 56.7, 56.5, 56.3, 56.1, 54.1, 51.8, 51.7, 51.1, 42.5, 35.7, 28.8, 28.5; MS (FAB, NBA) 999 (MH$^+$); HRMS (FAB, NBA) calcd for $C_{49}H_{67}N_4O_{18}$ (MH$^+$) 999.4451. found 999.4498.

General Procedure for Reductive Amination of Aldehyde 21 and Synthesis of Compounds 22–24

A solution of the corresponding mono-Cbz-alkylenedi-amine (5 equivalent) in methanol (1 mL) was acidified with a 1 M methanolic solution of acetic acid (~4 mL) to pH ~6 (pH paper). This solution was added to a solution of the crude aldehyde (~400 mg, 0.400 mmol) in methanol (3 mL) at room temperature. The mixture was subsequently treated with NaCNBH$_3$ (100 mg, 1.6 mmol) and stirred at ambient temperature for 2 h. The reaction mixture was diluted with ethylacetate, extracted with 1 N NaOH, water and then with brine. The organic layer was dried (Na$_2$SO$_4$) and concentrated to dryness in vacuo to give a solid, which was purified on a column (SiO$_2$, 19:1 CHCl$_3$/MeOH) to afford the corresponding aminated product as a white solid. The reported yields are for the combined two steps of ozonolysis and reductive amination.

6-O-[2-N-[2-(benzyloxycarbonyl)ethylamino]ethy-lamino]-3,2',6'-Tris(N-benzyloxycarbonyl)-1-N-tert-butoxylcarbonyl-5,3',4'-tri-O-methoxymethylneam-ine (22)

Yield (258 mg, 55%); R$_f$ 0.14 (19:1 CHCl$_3$/MeOH); mp 126–28° C.; FTIR (film): 3332, 3064, 2939, 2898, 2825, 1716, 1532, 1455, 1252, 1150, 1044, 1025 cm$^{-1}$; $^1$H NMR (400 MHz, pyridine-d$_5$) δ 8.35 (d, J=8.8 Hz, 1H, NH), 8.18 (s, 1H, NH), 8.06 (d, J=7.2 Hz, 1H, NH), 7.84 (s, 1H, NH), 7.56–7.31 (m, 20H), 5.79 (s, 1H), 5.53 (d, J=12.0 Hz, 1H), 5.38 (d, J=4.8 Hz, 2H), 5.32 (s, 3H), 5.27 (d, J=7.6 Hz, 2H), 5.07 (d, J=4.8 Hz, 1H), 5.04 (s, 2H), 4.99 (d, J=5.6 Hz, 1H), 4.90 (d, J=5.6 Hz, 1H), 4.83 (d, J=4.8 Hz, 1H), 4.48 (s,1H), 4.40 (t, J=9.6 Hz, 2H), 3.75 (s, 2H), 3.58 (s, 2H), 3.48 (s, 3H), 3.41 (s, 4H), 3.36 (s, 4H), 2.90–2.86 (m, 4H), 2.42 (br s, 1H, H2$_{eq}$), 1.80 (q, J=12.0 Hz, 1H, H2$_{ax}$), 1.52 (s, 9H); $^{13}$C NMR (100 MHz, pyridine-d$_5$) δ 157.3, 157.2, 157.1, 156.7, 156.3, 138.0, 137.8 (2C), 137.7, 128.8, 128.7, 128.5, 128.2, 128.1, 128.0, 99.2 (CH$_2$OCH$_3$), 99.1 (C1'), 98.8 (CH$_2$OCH$_3$), 98.4 (CH$_2$OCH$_3$), 84.1, 83.5, 79.8, 78.8, 78.4, 72.2 (CH$_2$), 70.7, 66.7 (CH$_2$Ph), 66.6 (CH$_2$Ph), 66.3 (CH$_2$Ph), 66.2 (CH$_2$Ph), 56.6 (CH$_2$OCH$_3$), 56.3 (CH$_2$OCH$_3$), 55.9 (CH$_2$OCH$_3$), 55.8, 51.2, 50.8, 50.3 (CH$_2$), 49.6 (CH$_2$), 42.2 (CH$_2$), 41.3 (CH$_2$), 35.4 (CH$_2$), 28.5 (CH$_3$); MS (FAB, NBA) 1177 (MH$^+$); HRMS (FAB, NBA) calcd for $C_{59}H_{81}N_6O_{19}$ (MH$^+$) 1177.5560. found 1177.5515.

6-O-[2-N-[3-(benzyloxycarbonyl)propylamino]ethy-lamino]-3,2',6'-Tris(N-benzyloxycarbonyl)-1-N-tert-butoxylcarbonyl-5,3',4'-tri-O-methoxymethylneam-ine (23)

Yield (318 mg, 67%); R$_f$ 0.15 (19:1 CHCl$_3$/MeOH); mp 71–73° C.; FTIR (film): 3329, 2932, 1716, 1531, 1455, 1253, 1149, 1026 cm$^{-1}$; $^1$H NMR (400 MHz, pyridine-d$_5$) δ

8.44 (d, J=8.8 Hz, 1H, NH), 8.24–8.16 (m, 4H, NH), 7.70 (s, 1H, NH), 7.49–7.28 (m, 20H), 5.81 (s, 1H), 5.56 (d, J=12.0 Hz, 1H), 5.43–5.24 (m, 7H), 5.08 (d, J=5.6 Hz, 1H), 5.05 (s, 2H), 5.00 (d, J=5.6 Hz, 1H), 4.90 (d, J=5.6 Hz, 1H), 4.84 (d, J=5.6 Hz, 1H), 4.51 (s,1H), 4.42 (t, J=10.0 Hz, 1H), 4.31 (t, J=9.2 Hz, 1H), 4.09–3.78 (m, 9H), 3.54 (ABq, J=14.2, 5.6 Hz, 2H), 3.48 (s, 3H), 3.41 (s, 3H), 3.38 (s, 1H), 3.35 (s, 3H), 2.95–2.90 (m, 3H), 2.39 (br s, 1H, H2$_{eq}$), 2.01 (br s, 2H), 1.85 (q, J=12.4 Hz, 1H, H2$_{ax}$), 1.52 (s, 9H), 1.36–1.26 (m, 1H); $^{13}$C NMR (100 MHz, pyridine-d$_5$) δ 157.4, 157.3, 157.2, 156.7, 156.3, 138.1, 137.8 (2C), 128.8, 128.7, 128.5, 128.3, 128.2, 128.1, 128.0, 99.4 (CH$_2$OCH$_3$), 99.1 (C1'), 98.8 (CH$_2$OCH$_3$), 98.4 (CH$_2$OCH$_3$), 84.1, 79.6, 78.8, 78.3, 70.7 (CH$_2$), 66.7 (CH$_2$Ph), 66.6 (CH$_2$Ph), 66.3 (CH$_2$Ph), 66.2 (CH$_2$Ph), 56.7 (CH$_2$OCH$_3$), 56.4 (CH$_2$OCH$_3$), 55.9 (CH$_2$OCH$_3$), 55.8, 51.1, 50.7, 50.0 (CH$_2$), 46.9 (CH$_2$), 42.1 (CH$_2$), 39.2 (CH$_2$), 35.5 (CH$_2$), 29.9 (CH$_2$), 29.6 (CH$_2$), 28.5 (CH$_3$); MS (FAB, NBA) 1191 (MH$^+$); HRMS (FAB, NBA) calcd for C$_{60}$H$_{83}$N$_6$O$_{19}$ (MH$^+$) 1191.5710. found 1191.5660.

6-O-[2-N-[4-(benzyloxycarbonyl)butylamino]ethylamino]-3,2',6'-Tris(N-benzyloxycarbonyl)-1-N-tert-butoxylcarbonyl-5,3',4'-tri-O-methoxymethylneamine (24)

Yield (311 mg, 63%); R$_f$ 0.17 (19:1 CHCl$_3$/MeOH); mp 66–68° C.; FTIR (film): 3329, 3033, 2940, 2902, 2825, 1708, 1529, 1455, 1254, 1148, 1028 cm$^{-1}$; $^1$H NMR (500 MHz, pyridine-d$_5$) δ 8.36 (d, J=9.0 Hz, 1H, NH), 8.18–8.10 (m, 4H, NH), 7.56–7.30 (m, 20H), 5.76 (s, 1H), 5.54 (d, J=12.0 Hz, 1H), 5.42–5.23 (m, 7H), 5.06 (d, J=5.5 Hz, 1H), 5.00 (d, J=4.5 Hz, 1H), 4.96–4.94 (m, 2H), 4.86 (d, J=6.5 Hz, 1H), 4.83 (d, J=6.5 Hz, 1H), 4.49 (d, J=9.0 Hz, 1H), 4.38 (td, J=10.5, 3.0 Hz, 1H), 4.26 (t, J=10.0 Hz, 1H), 4.16–3.94 (m, 5H), 3.86 (t, J=9.5 Hz, 1H), 3.81–3.72 (m, 2H), 3.50–3.23 (m, 14H), 3.10 (s, 2H), 2.29 (d, J=10.5 Hz, 1H, H2$_{eq}$), 1.92–1.84 (m, 3H), 1.76 (quint, J=7.0 Hz, 2H), 1.51 (s, 9H), 1.50–1.46 (m, 1H); $^{13}$C NMR (125 MHz, pyridine-d$_5$) δ 157.4, 157.3, 157.1, 156.7, 156.4, 138.0, 137.7 (2C), 128.8, 128.7, 128.6, 128.3, 128.2, 128.1, 99.6 (CH$_2$OCH$_3$), 99.0 (C1'), 98.8 (CH$_2$OCH$_3$), 98.4 (CH$_2$OCH$_3$), 84.4, 84.2, 79.4, 78.8, 78.3, 70.6 (CH$_2$), 66.7 (CH$_2$Ph), 66.6 (CH$_2$Ph), 66.3 (CH$_2$Ph), 66.1 (CH$_2$Ph), 56.5 (CH$_2$OCH$_3$), 56.3 (CH$_2$OCH$_3$), 55.9 (CH$_2$OCH$_3$), 55.7, 51.0, 50.6, 48.8 (CH$_2$), 48.0 (CH$_2$), 42.0 (CH$_2$), 40.6 (CH$_2$), 35.4 (CH$_2$), 28.4 (CH$_3$), 29.8 (CH$_2$), 27.9 (CH$_2$), 25.1(CH$_2$); MS (FAB, NBA) 1205 (MH$^+$); HRMS (FAB, NBA) calcd for C$_{61}$H$_{85}$N$_6$O$_{19}$ (MH$^+$) 1205.5870. found 1205.5821.

6-O-[2-N-[2-(benzyloxycarbonyl)ethylamino]ethylamino]-3,2',6'-Tris(N-benzyloxycarbonyl)neamine (25)

To a solution of 22 (145 mg, 0.123 mmol) in chloroform (2 mL) was added a solution of 2 N hydrochloric acid in methanol (4 mL) and the mixture was kept at room temperature for 12 h. The reaction mixture was quenched with triethylamine and concentrated to dryness in vacuo to give a solid as the crude product. The solid was washed with ether, suspended in water, filtered and purified on a column (SiO$_2$, 15:2:0.1 CHCl$_3$/MeOH/NH$_4$OH) to give 25 (85 mg, 73%) as a pure white solid. R$_f$ 0.17 (15:2:0.2 CHCl$_3$/MeOH/NH$_4$OH); mp 193–95° C.; FTIR (KBr): 3401, 3332, 3063, 2935, 1697, 1536, 1454, 1261, 1139, 1052, 1015, 735, 697 cm$^{-1}$; $^1$H NMR (500 MHz, DMSO-d$_6$) δ 7.35–7.28 (m, 20H), 7.20–7.18 (m, 2H, NH), 6.94 (s, 2H, NH), 5.09 (s, 1H), 5.06–4.99 (m, 8H), 4.89 (d, J=12.0 Hz, 1H), 3.73 (d, J=4.5 Hz, 1H), 3.68–3.62 (m, 2H), 3.47–3.42 (m, 4H), 3.37 (t, J=9.0 Hz, 1H), 3.34 (t, J=9.5 Hz, 1H), 3.16–3.10 (m, 2H), 3.05 (q, J=6.0 Hz, 2H), 2.69 (t, J=8.5 Hz, 1H), 2.62–2.49 (m, 4H), 1.71 (d, J=10.5 Hz, 1H, H2$_{eq}$), 1.22–1.17 (m, 1H, H2$_{ax}$); $^{13}$C NMR (125 MHz, DMSO-d$_6$) δ 157.2, 156.9, 156.8, 156.5, 138.1, 137.9, 137.7, 129.0 (2C), 128.9, 128.5, 128.4, 128.3 (2C), 128.1, 127.9, 99.4 (C1'), 87.9, 83.3, 76.2, 72.1, 71.8, 71.5 (CH$_2$), 71.4, 66.1 (CH$_2$Ph), 66.0 (CH$_2$Ph), 65.9 (CH$_2$Ph), 65.8 (CH$_2$Ph), 56.9, 51.2, 51.1, 49.3 (CH$_2$), 49.0 (CH$_2$), 42.7 (CH$_2$), 40.7 (CH$_2$), 37.2 (CH$_2$); MS (FAB, Gly) 945 (MH$^+$); HRMS (FAB, Gly) calcd for C$_{48}$H$_{61}$N$_6$O$_{14}$ (MH$^+$) 945.4246. found 945.4248.

6-O-[2-N-[3-(benzyloxycarbonyl)propylamino]ethylamino]-3,2',6'-Tris(N-benzyloxycarbonyl)neamine (26)

A solution of 23 (260 mg, 0.218 mmol) in chloroform (3 mL) was treated with a solution of 2 N hydrochloric acid in methanol (6 mL), as described for 25. Yield (182 mg, 87%). R$_f$ 0.18 (15:2:0.2 CHCl$_3$/MeOH/NH$_4$OH); mp 253–55° C.; FTIR (KBr): 3422, 3344, 3062, 3032, 2927, 2881, 1693, 1536, 1287, 1262, 1048 cm$^{-1}$; $^1$H NMR (400 MHz, DMSO-d$_6$) δ 7.35–7.30 (m, 20H), 6.93 (s, 2H, NH), 6.69 (s, 2H, NH), 5.09 (s, 1H), 5.06–5.00 (m, 8H), 4.88 (d, J=11.6 Hz, 1H), 4.08 (s, 1H), 3.85 (s, 1H), 3.61 (s, 1H), 3.53 (t, J=9.2 Hz, 2H), 3.44–3.37 (m, 4H), 3.31 (t, J=9.6 Hz, 1H), 3.12–3.02 (m, 6H), 2.85 (d, J=4.8 Hz, 2H), 1.96 (s, 1H, H2$_{eq}$), 1.80 (t, J=6.4 Hz, 2H), 1.51 (q, J=11.6, 1H, H2$_{ax}$); $^{13}$C NMR (100 MHz, DMSO-d$_6$) δ 157.2, 156.8 (2C), 156.4, 138.0, 137.9, 137.8, 137.6, 129.0 (2C), 128.9, 128.4, 128.3 (2C), 128.2, 128.0, 99.3 (C1'), 82.2, 76.3, 72.1, 71.7, 71.2, 67.9 (CH$_2$), 66.2 (CH$_2$Ph), 66.0 (2C, CH$_2$Ph), 65.9 (CH$_2$Ph), 56.8, 50.4, 49.3, 47.7 (CH$_2$), 45.5 (CH$_2$), 42.6 (CH$_2$), 38.4 (CH$_2$), 32.9 (CH$_2$), 27.0 (CH$_2$); MS (FAB, Gly) 959 (MH$^+$); HRMS (FAB, Gly) calcd for C$_{49}$H$_{63}$N$_6$O$_{14}$ (MH$^+$) 959.4402. found 959.4403.

6-O-[2-N-[4-(benzyloxycarbonyl)butylamino]ethylamino]-3,2',6'-Tris(N-benzyloxycarbonyl)neamine (27)

A solution of 24 (318 mg, 0.264 mmol) in chloroform (4 mL) was treated with a solution of 2 N hydrochloric acid in methanol (8 mL), as described for 25. Yield (191 mg, 74%). R$_f$ 0.18 (15:2:0.2 CHCl$_3$/MeOH/NH$_4$OH); mp 225–27° C.; FTIR (KBr): 3400, 3341, 3027, 2930, 1695, 1535, 1456, 1259, 1140, 1266, 1044 cm$^{-1}$; $^1$H NMR (500 MHz, DMSO-d$_6$) δ 7.36–7.28 (m, 20H), 6.99 (s, 2H, NH), 6.92 (d, J=6.5 Hz, 2H, NH), 5.12 (s, 1H), 5.07–4.98 (m, 8H), 4.89 (d, J=12.5 Hz, 1H), 3.79 (s, 2H), 3.65 (s, 1H), 3.48–3.37 (m, 4H), 3.36 (q, J=9.0 Hz, 1H), 3.16–3.13 (m, 2H), 2.98 (s, 2H), 2.92 (t, J=9.0 Hz, 1H), 2.77 (t, J=7.0 Hz, 1H), 2.70 (s, 2H), 2.53 (s, 2H), 1.81 (d, J=8.5 Hz, 1H, H2$_{eq}$), 1.40–1.34 (m, 5H); $^{13}$C NMR (125 MHz, DMSO-d$_6$) δ 157.2, 156.9, 156.8, 156.5, 138.0 (2C), 137.9, 137.7, 129.0, 128.5, 128.4, 128.3, 128.0, 99.3 (C1'), 85.3, 82.7, 76.2, 72.1, 71.8, 71.4, 69.7 (CH$_2$), 66.1 (CH$_2$Ph), 66.0 (CH$_2$Ph), 65.8 (2C, CH$_2$Ph), 56.8, 50.9, 50.6, 48.5 (CH$_2$), 48.2 (CH$_2$), 42.7 (CH$_2$), 40.7 (CH$_2$), 36.1 (CH$_2$), 27.7 (CH$_2$), 25.9 (CH$_2$); MS (FAB NBA) 973 (MH$^+$); HRMS (FAB, NBA) calcd for C$_{50}$H$_{65}$N$_6$O$_{14}$ (MH$^+$) 973.4559. found 973.4515.

N-[(S)-4-(Benzyloxycarbonylamino)-2-hydroxybutanoyloxy]succinimide (28)

A mixture of the N-Cbz protected (S)-4-amino-2-hydroxybutanoic acid (76 mg, 0.300 mmol, prepared from treatment of 1.0 eq. of the acid with 1.2 eq. of benzyl chloroformate in the presence of 2.1 equiv. of sodium carbonate at 0–5° C. overnight, $[\alpha]_D^{25}=-61°$), N-hydroxysuccinimide (38 mg, 0.318 mmol), and DCC (63 mg, 0.300 mmol) in anhydrous THF (3.5 mL) was stirred at room temperature under an atmosphere of argon for 2 h. This solution was directly used for the syntheses of 29–31.

General Procedure for Synthesis of 29–31

A solution of the starting material (100 mg, ~0.104 mmol) was made in 3:1 dioxane-water (4 mL). To this solution was added a saturated solution of NaHCO$_3$ (100 µL) and a solution of 28 (2.5 mL 0.086 M in anhydrous THF, 0.215 mmol) and the mixture was stirred at room temperature for 2 h. The reaction mixture was concentrated to dryness in vacuo. The resultant residue was suspended in water, filtered and washed with water to give a white solid as a crude product. The solid was dissolved in 3:1 CHCl$_2$/MeOH, pre-absorbed on silica gel (~1 g), dried and purified on a column (SiO$_2$, 15:2:0.1 CHCl$_3$/MeOH/NH$_4$OH) to afford the product as a pure white solid.

1-N-[(S)-4-(Benzyloxycarbonylamino)-2-hydroxybutanoyl]-6-O-[2-N-(2-(benzyloxycarbonyl)ethylamino]ethylamino]-3,2',6'-Tris(N-benzyloxycarbonyl)neamine (29)

Yield (63 mg, 50%); R$_f$ 0.36 (15:3:0.2 CHCl$_3$/MeOH/NH$_4$OH); mp 223–25° C.; FTIR (KBr): 3414, 3326, 3064, 3033, 2942, 1686, 1531, 1454, 1263, 1140, 1053, 1015, 736, 969 cm$^{-1}$; $^1$H NMR (400 MHz, pyridine-d$_5$) δ 8.62 (s, 1H, NH), 8.28 (d, J=8.0 Hz, 1H, NH), 8.21 (s, 1H, NH), 8.14 (s, 1H, NH), 7.91 (s, 1H, NH), 7.81 (s, 1H, NH), 7.56–7.28 (m, 25H), 6.02 (s, 1H), 5.53 (d, J=12.0 Hz, 1H), 5.36–5.19 (m, 10H), 4.71 (s, 1H), 4.64 (s, 1H), 4.58–4.46 (m, 2H), 4.33 (s, 1H), 4.14–4.02 (m, 5H), 3.95–3.80 (m, 3H), 3.70 (t, J=8.8 Hz, 1H), 3.65–3.52 (m, 3H), 2.80–2.72 (m, 3H), 2.58 (s,1H), 2.40–2.30 (m, 2H), 2.10–2.04 (m, 1H), 1.27 (br s, 1H); $^{13}$C NMR (100 MHz, pyridine-d$_5$) δ 174.7, 157.8 (2C), 157.4, 157.3, 156.8, 138.0, 137.9, 137.8, 128.7, 128.6, 128.4, 128.2, 128.1, 128.0, 127.9, 100.6 (C1'), 84.5, 83.1, 77.0, 73.2, 72.9, 72.5, 70.8 (CH$_2$), 70.4, 66.5 (CH$_2$Ph), 66.3 (2C, CH$_2$Ph), 66.1 (2C, CH$_2$Ph), 57.8, 51.3, 49.4 (CH$_2$), 49.3, 49.1 (CH$_2$), 42.8 (CH$_2$), 40.7 (CH$_2$), 38.3 (CH$_2$), 35.8 (CH$_2$), 35.2 (CH$_2$); MS (FAB, NBA) 1180 (MH$^+$); HRMS (FAB, NBA) calcd for C$_{60}$H$_{74}$N$_7$O$_{18}$ (MH$^+$) 1180.5090. found 1180.5084.

1-N-[(S)-4-(Benzyloxycarbonylamino)-2-hydroxybutanoyl]-6-O-[2-N-[3-(benzyloxycarbonyl)propylamino]ethylamino]-3,2',6'-Tris(N-benzyloxycarbonyl)neamine (30)

Yield (58 mg, 46%); R$_f$ 0.36 (15:3:0.2 CHCl$_3$/MeOH/NH$_4$OH); mp 201–203° C.; FTIR (KBr): 3328, 2929, 1695, 1532, 1261, 1027, cm$^{-1}$; $^1$H NMR (400 MHz, pyridine-d$_5$) δ 8.62 (d, J=7.2 Hz, 1H, NH), 8.33 (d, J=8.0 Hz, 1H, NH), 8.23 (s, 1H, NH), 8.16 (d, J=6.4 Hz, 1H, NH), 7.98 (s, 1H, NH), 7.83 (s, 1H, NH), 7.56–7.26 (m, 25H), 6.04 (s, 1H), 5.53 (d, J=12.8 Hz, 1H), 5.34–5.21 (m, 10H), 4.71 (t, J=2.4 Hz, 1H), 4.64 (s, 1H), 4.55 (q, J=8.8 Hz, 1H), 4.50 (q, J=9.2 Hz, 1H) 4.34 (s, 1H), 4.18–4.05 (m, 5H), 3.96–3.88 (m, 3H), 3.80 (t, J=5.6 Hz, 1H), 3.72 (t, J=9.6 Hz, 1H), 3.42 (q, J=5.6 Hz, 2H), 2.71 (s,1H), 2.62 (s,3H), 2.40–2.31 (m, 2H), 2.06 (q, J=11.6 Hz, 1H), 1.84 (s, 2H), 1.33–1.27 (m, 1H); $^{13}$C NMR (100 MHz, pyridine-d$_5$) δ 174.8, 157.8 (2C), 157.3, 156.8 (2C), 138.1, 138.0, 137.9, 128.7, 128.6, 128.4, 128.2, 128.1, 128.0, 127.8, 100.5 (C1'), 84.4, 82.9, 77.0, 73.1, 72.9, 72.5, 70.7 (CH$_2$), 70.4, 67.1 (CH$_2$Ph), 66.5 (CH$_2$Ph), 66.3 (CH$_2$Ph), 66.1 (2C, CH$_2$Ph), 57.7, 51.3, 49.6 (CH$_2$), 49.3, 46.8 (CH$_2$), 42.8 (CH$_2$), 39.2 (CH$_2$), 38.3 (CH$_2$), 35.8 (CH$_2$), 35.2 (CH$_2$), 29.9 (CH$_2$); MS (FAB, NBA) 1194 (MH$^+$); HRMS (FAB, NBA) calcd for C$_{61}$H$_{76}$N$_7$O$_{18}$ (MH$^+$) 1194.5250. found 1194.5246.

1-N-[(S)-4-(Benzyloxycarbonylamino)-2-hydroxybutanoyl]-6-O-[2-N-[4-(benzyloxycarbonyl)butylamino]ethylamino]-3,2',6'-Tris(N-benzyloxycarbonyl)neamine (31)

Yield (67 mg, 54%); R$_f$ 0.37 (15:3:0.2 CHCl$_3$/MeOH/NH$_4$OH); mp 207–209° C.; FTIR (KBr): 3318, 3064, 2933, 1712, 1686, 1535, 1454, 1267, 1140, 1055, 1016 cm$^{-1}$; $^1$H NMR (500 MHz, pyridine-d$_5$) δ 8.61 (d, J=8.0 Hz, 1H, NH), 8.31 (d, J=8.0 Hz, 1H, NH), 8.17 (t, J=5.5 Hz, 1H, NH), 8.10 (d, J=7.5 Hz, 1H, NH), 7.92 (t, J=5.5 Hz, 1H, NH), 7.77 (s, 1H, NH), 7.55–7.27 (m, 25H), 6.02 (s, 1H), 5.53 (d, J=13.0 Hz, 1H), 5.38–5.19 (m, 10H), 4.70 (q, J=4.0 Hz, 1H), 4.63 (s, 1H), 4.53 (q, J=9.0 Hz, 1H), 4.50 (qd, J=9.0, 3.0 Hz, 1H) 4.34 (d, J=10.0 Hz, 1H, NH), 4.15–3.97 (m, 6H), 3.91–3.87 (m, 2H), 3.80 (q, J=6.0 Hz, 1H), 3.72 (t, J=9.5 Hz, 1H), 3.36 (s, 2H), 2.74–2.53 (m,5H), 2.38–2.32 (m, 2H), 2.06 (q, J=12.0 Hz, 1H), 1.60 (br s, 4H); $^{13}$C NMR (125 MHz, pyridine-d$_5$) δ 174.7, 157.8 (2C), 157.4, 157.2, 156.8, 138.2, 138.0, 137.9, 128.7, 128.6, 128.4, 128.1, 128.0, 127.9, 100.5 (C1'), 84.5, 83.1, 77.0, 73.0, 72.9, 72.5, 70.5 (CH$_2$), 70.4, 66.5 (CH$_2$Ph), 66.3 (2C, CH$_2$Ph), 66.1 (2C, CH$_2$Ph), 57.7, 51.3, 49.5 (CH$_2$), 49.3, 48.9 (CH$_2$), 42.8 (CH$_2$), 41.1 (CH$_2$), 38.3 (CH$_2$), 35.8 (CH$_2$), 35.2 (CH$_2$), 28.0 (CH$_2$), 26.6 (CH$_2$); MS (FAB, NBA) 1208 (MH$^+$); HRMS (FAB, NBA) calcd for C$_{62}$H$_{78}$N$_7$O$_{18}$ (MH$^+$) 1208.5400. found 1208.5392.

General Procedure for Deprotection of Compounds 29–31 and 26

To a solution of the Cbz protected compound in glacial acetic acid (~0.05 mmol/ml) was added palladium (Pd) on activated carbon (10%, 3-fold excess by weight; e.g., 90 mg for 30 mg of the starting compound). To this mixture was added 1,4-cyclohexadiene (10 mole equivalent per each protecting group in the compound) and the mixture was allowed to stir at ambient temperature under an atmosphere of argon for 4 h. The reaction mixture was filtered (Celite), the filter-cake was thoroughly washed with water and the filtrate was concentrated to dryness in vacuo. The crude product was purified on a short column (Amberlite CG-50 ion-exchange resin, NH4$^+$ form, 3×1 cm) using 0.2–1.0 M aqueous ammonia as eluent. Fractions containing the product were pooled and concentrated to dryness in vacuo and the resultant residue was dissolved in 0.1 N aqueous hydrochloric acid (1–2 mL) and lyophilized to give the product as hydrochloride salt. Analytical samples for NMR spectroscopy were prepared by dissolving the solids in D$_2$O and lyophilizing them again (this process was repeated twice). The reported yields are based on the hydrochloride salts.

1-N-[(S)-4-Amino-2-hydroxybutanoyl]-6-O-[2-N-(2-ethylamino)ethylamino]neamine (3)

Yield (10 mg, 51%) (based on 32 mg of 29); $R_f$ 0.06 (9:4:4 MeOH/H$_2$O/NH$_4$OH, cf. neamine 1: $R_f$ 0.52); FTIR (KBr): 3394 (br), 2994 (br), 1604, 1497, 1395, 1123, 1058, 1029, 579 cm$^{-1}$; $^1$H NMR (500 MHz, D$_2$O) δ 5.77 (d, J=4.0 Hz, 1H, H1'), 4.15 (dd, J=10.0, 3.5 Hz, 1H), 3.94–3.79 (m, 6H), 3.70 (t, J=9.0 Hz, 1H), 3.41–3.35 (m, 2H), 3.34 (ABq, J=9.5, 6.0 Hz, 2H), 3.31–3.25 (m, 5H), 3.23–3.20 (m, 1H), 3.14 (ABq, J=13.5, 7.0 Hz, 2H), 3.02 (t, J=7.5 Hz, 2H), 2.08 (dt, J=12.5, 4.0 Hz, 1H, H2$_{eq}$), 2.03 (m, J=3.5 Hz, 1H), 1.76 (qd, J=9.5, 2.5 Hz, 1H), 1.73 (q, J=12.5 Hz, 1H, H2$_{ax}$); $^{13}$C NMR (125 MHz, D$_2$O) δ 176.6, 96.1 (C1'), 82.8, 78.0, 75.3, 70.8, 69.6, 69.3, 68.3, 67.3 (CH$_2$), 53.7, 48.9, 48.3 (CH$_2$), 48.1, 44.3 (CH$_2$), 40.2 (C6'), 37.0 (CH$_2$), 35.5 (CH$_2$), 31.1 (CH$_2$), 30.2 (C2); MS (FAB, NBA) 509 (M$^+$); HRMS (FAB, NBA) calcd for C$_{20}$H$_{44}$N$_7$O$_8$ (MH$^+$) 510.3250. Found 510.323%.

1-N-[(S)-4-Amino-2-hydroxybutanoyl]-6-O-[2-N-(3-propylamino)ethylamino]neamine (4)

Yield (11 mg, 52%) (based on 34 mg of 30); $R_f$ 0.06 (9:4:4 MeOH/H$_2$O/NH$_4$OH); FTIR (KBr): 3378 (br), 2976 (br), 1647, 1605, 1497, 1398, 1122, 1057, 1031, 575 cm$^{-1}$; $^1$H NMR (500 MHz, D$_2$O) δ 5.80 (d, J=2.5 Hz, 1H, H1'), 4.17 (dd, J=9.5, 1.5 Hz, 1H), 3.97–3.80 (m, 6H), 3.71 (t, J=9.5 Hz, 1H), 3.43–3.34 (m, 5H), 3.20–3.15 (m, 2H), 3.10 (d, J=7.0 Hz, 1H), 3.07–3.04 (m, 4H), 2.98 (t, J=7.5 Hz, 2H), 2.11 (dt, J=13.5, 4.5 Hz, 1H, H2$_{eq}$), 2.07–2.03 (m, 1H), 1.98 (quint, J=7.5 Hz, 2H), 1.83–1.75 (m, 1H), 1.74 (q, J=13.0 Hz, 1H, H2$_{ax}$); $^{13}$C NMR (125 MHz, D$_2$O) δ 175.6, 96.2 (C1'), 82.9, 78.1, 75.3, 70.9, 69.7, 69.4, 68.4, 67.4 (CH$_2$), 53.7, 49.0, 48.1, 47.9 (CH$_2$), 44.8 (CH$_2$), 40.3 (C6'), 37.1 (CH$_2$), 36.7 (CH$_2$), 31.1 (CH$_2$), 30.2 (C2), 23.8 (CH$_2$); MS (FAB, NBA) 523 (M$^+$); HRMS (FAB, NBA) calcd for C$_{21}$H$_{46}$N$_7$O$_8$ (MH$^+$) 524.3407. Found 524.3404.

1-N-[(S)-4-Amino-2-hydroxybutanoyl]-6-O-[2-N-(4-butylamino)ethylamino]neamine (5)

Yield (27 mg, 68%) (based on 63 mg of 31); $R_f$ 0.06 (9:4:4 MeOH/H$_2$O/NH$_4$OH); FTIR (KBr): 3410 (br), 2976 (br), 1652, 1647, 1616, 1506, 1124, 1056, 1029, 576 cm$^{-1}$; $^1$H NMR (500 MHz, D$_2$O) δ 5.80 (s, 1H, H1'), 4.17 (dd, J=9.5, 3.0 Hz, 1H), 3.93–3.82 (m, 6H), 3.71 (t, J=9.5 Hz, 1H), 3.42–3.34 (m, 5H), 3.16 (ABq, J=14.0, 6.5 Hz, 2H), 3.08–3.03 (m, 3H), 2.99 (t, J=6.5 Hz, 2H), 2.90 (t, J=6.5 Hz, 2H), 2.09 (dt, J=13.0, 5.0 Hz, 1H, H2$_{eq}$), 2.05–2.01 (m, J=3.5 Hz, 1H), 1.82–1.70 (m, 2H), 1.64 (s, 4H); $^{13}$C NMR (125 MHz, D$_2$O) δ 175.6, 96.1 (C1'), 82.9, 78.1, 75.3, 70.1, 69.8, 69.4, 68.5, 67.4 (CH$_2$), 53.8, 49.1, 48.2, 47.8 (CH$_2$), 47.2 (CH$_2$), 40.4 (C6'), 39.1 (CH$_2$), 37.2 (CH$_2$), 31.2 (CH$_2$), 30.3 (C2), 24.2 (CH$_2$), 22.9 (CH$_2$); MS (FAB, NBA) 537 (M$^+$); HRMS (FAB, NBA) calcd for C$_{22}$H$_{48}$N$_7$O$_8$ (MH$^+$) 538.3563. found 538.3566.

6-O-[2-N-(3-Propylamino)ethylamino]neamine (6)

Yield (6 mg, 44%) (based on 20 mg of 26); $R_f$ 0.08 (9:4:4 MeOH/H$_2$O/NH$_4$OH); FTIR (KBr): 3394 (br), 2982 (br), 1601, 1497, 1457, 1410, 1124, 1058, 1026, 540 cm$^{-1}$; $^1$H NMR (500 MHz, D$_2$O) δ 5.76 (d, J=3.5 Hz, 1H, H1'), 4.10 (dd, J=11.0, 6.0 Hz, 1H), 3.90–3.82 (m, 4H), 3.76 (t, J=9.0 Hz, 1H), 3.46 (t, J=9.5 Hz, 1H), 3.42–3.29 (m, 5H), 3.21 (s, 2H), 3.14 (dd, J=13.5, 6.5 Hz, 1H), 3.04 (t, J=8.0 Hz, 2H), 2.94 (t, J=8.0 Hz, 2H), 2.35 (dt, J=12.0, 4.5 Hz, 1H, H2$_{eq}$), 1.96 (quint, J=8.0 Hz, 2H), 1.78 (q, J=12.5 Hz, 1H, H2$_{ax}$); $^{13}$C NMR (125 MHz, D$_2$O) δ 96.1 (C1'), 80.8, 77.4, 75.6, 70.7, 69.4, 68.2, 67.9 (CH$_2$), 53.6, 48.8, 48.4, 47.9 (CH$_2$), 44.9 (CH$_2$), 40.2 (C6'), 36.7 (CH$_2$), 28.3 (C2), 23.8 (CH$_2$); MS (FAB, NBA) 422 (M$^+$); HRMS (FAB, NBA) calcd for C$_{17}$H$_{39}$N$_6$O$_6$ (MH$^+$) 423.2930. found 423.2941.

1-N,6-O-(2-N)-Bis[(S)-4-(benzyloxycarbonylamino)-2-hydroxybutanoyl]-6-O-[2-N-[3-(benzyloxycarbonyl)propylamino]ethylamino]-3,2',6'-Tris(N-benzyloxycarbonyl)neamine (32)

To a solution of 30 (60 mg, 0.050 mmol) in anhydrous pyridine (200 μL) was added dropwise a solution of 28 in anhydrous THF (0.5 mL 0.450 M, 0.225 mmol) and the mixture was stirred at room temperature for 1 h. The reaction mixture was diluted with water and extracted with methylene chloride (3×10 mL). The organic layer was back extracted with brine, dried (Na$_2$SO$_4$) and concentrated to dryness in vacuo. The resultant solid was purified on a column (SiO$_2$, 14:1:0.1 CHCl$_3$/MeOH/NH$_4$OH) to afford recovered starting compound (22 mg, 37%) and 32 (19 mg, 26%); $R_f$ 0.67 (15:3:0.2 CHCl$_3$/MeOH/NH$_4$OH); mp 228–30° C.; FTIR (KBr): 3328, 2930, 1699, 1653, 1533, 1437, 1260, 1136, 1028, 737, 696 cm$^{-1}$; $^1$H NMR (400 MHz, pyridine-d$_5$) δ 8.30 (d, J=8.0 Hz, 1H, NH), 8.22–8.18 (m, 3H, NH), 7.87–7.79 (m, 3H, NH), 7.56–7.27 (m, 30H), 6.19 (d, J=9.2 Hz, 1H), 6.05 (s, 1H), 5.54 (d, J=12.0 Hz, 1H), 5.34–5.17 (m, 12H), 5.12–488 (m, 2H), 4.65 (s, 2H), 4.53 (s, 3H), 4.22–3.98 (m, 7H) 3.92–3.76 (m, 3H), 3.60–3.38 (m, 4H), 3.24–3.14 (m, 1H), 2.94 (d, J=15.2 Hz, 1H), 2.74 (td, J=10.4, 4.0 Hz, 1H), 2.64–2.56 (m, 1H), 2.42 (d, J=11.2 Hz, 1H), 2.33 (d, J=11.2 Hz, 1H), 19.2 (q, J=11.6 Hz, 1H), 1.80–1.71 (m, J=6.4 Hz, 2H), 1.28 (brs, 1H); $^{13}$C NMR (100 MHz, pyridine-d$_5$) δ 172.1, 159.3, 157.8, 157.7, 157.3, 156.8 (2C), 138.0, 137.9, 128.7, 128.6, 128.4, 128.2, 128.1, 128.0, 127.9, 100.8 (C1'), 85.9, 83.2, 78.9, 74.3 (CH$_2$), 72.8 (2C), 72.6, 70.4, 66.5 (CH$_2$Ph), 66.3 (2C, CH$_2$Ph), 66.2 (3C, CH$_2$Ph), 57.8, 51.5, 48.1, 47.6 (CH$_2$), 43.9 (CH$_2$), 42.8 (CH$_2$), 38.8 (CH$_2$), 38.3 (CH$_2$), 38.1 (CH$_2$), 35.9 (CH$_2$), 35.2 (CH$_2$), 29.9 (CH$_2$), 28.6 (CH$_2$); MS (FAB, NBA) 1451 (M+Na$^+$); HRMS (FAB, NBA) calcd for C$_{73}$H$_{88}$N$_8$O$_{22}$Na (M+Na$^+$) 1451.5910. found 1451.5950.

1-N,6-O-(2-N)-Bis[(S)-4-amino-2-hydroxybutanoyl]-6-O-[2-N-(3-propylamino)ethylamino]neamine (7)

To a solution of 32 (18 mg, 0.0125 mmol) in glacial acetic acid was added palladium (Pd) on activated carbon (60 mg, 10%) and the mixture was treated with 1,4-cyclohexadiene (60 μL, 0.646 mmol) at room temperature under an atmosphere of argon for 10 h. Purification of the mixture (as described for 3–5) gave the title compound (5.5 mg, 52%, a mixture of two rotamers by NMR) as a hydrochloride salt. $R_f$ 0.12 (9:4:4 MeOH/H$_2$O/NH$_4$OH); FTIR (KBr): 3409 (br), 2976 (br), 1648, 1492, 1120, 1060, 1027, 576 cm$^{-1}$; $^1$H NMR (500 MHz, D$_2$O) δ 5.76 (d, J=4.5 Hz, 1H, H1'), 4.14–4.09 (m, 1H), 3.86–3.77 (m, 5H), 3.73–3.58 (m, 3H), 3.38–3.29 (m, 8H), 3.26–3.16 (m, 2H), 3.13 (dd, J=12.0, 6.5 Hz, 1H), 3.01 (t, J=7.0 Hz, 3H), 2.94 (t, J=8.0 Hz, 1H), 2.81 (t, J=7.5 Hz, 1H), 2.08–2.04 (m, 1H), 2.02–1.96 (m, 1H), 1.87–1.62 (m, 4H); $^{13}$C NMR (125 MHz, D$_2$O) δ 175.6, 175.4, 96.2 (C1'), 83.0, 82.8, 82.5 (w), 82.2, 78.2 (w), 78.1, 77.5, 75.3, 70.8, 69.9 (CH$_2$), 69.6, 69.3, 68.3, 67.4 (CH$_2$), 53.6, 48.1 (w), 47.7 (w), 45.8 (w, CH$_2$), 45.1 (CH$_2$), 42.7 (CH$_2$), 40.2 (C6'), 39.6 (w, CH$_2$), 37.0 (CH$_2$), 36.9 (w, CH$_2$), 36.8 (CH$_2$), 35.8 (w, CH$_2$), 34.8 (CH$_2$), 31.2 (CH$_2$), 31.1 (w, CH$_2$), 30.3 (C2), 30.2 (w, C2), 25.8 (w, CH$_2$), 25.6 (CH$_2$), 25.0 (w, CH$_2$), 24.6 (CH$_2$); MS (FAB, NBA) 624 (M$^+$); HRMS (FAB, NBA) calcd for C$_{25}$H$_{53}$N$_8$O$_{10}$ (MH$^+$) 625.3884. found 625.3892.

The designated weak (w) signals in the $^{13}$C NMR spectrum belong to the minor rotamer.

N-[4-(Benzyloxycarbonylamino)phenylethanoyloxy]succinimide (33)

To an ice-cold solution of 4-aminophenylacetic acid (500 mg, 3.307 mmol) in 1:1 dioxane-water (10 mL) was added a solution of 2 N NaOH (~2.2 equivalent, pH 9–10). This mixture was treated with benzylchloroformate (0.5 mL, 3.681 mmol) and the solution was allowed to stir in an ice-bath for 2 h. The reaction mixture was acidified with an aqueous solution of 1 N HCl (pH ~4), extracted with ethyl acetate, dried (Na$_2$SO$_4$), and concentrated in vacuo to give a solid as crude product. Purification of the solid (SiO$_2$, 10:1 CHCl$_3$/MeOH) gave N-Cbz protected phenylacetic acid (856 mg, 91%) as a pure white solid. To make the succinimide active ester, a mixture of N-Cbz protected acid (120 mg, 0.421 mmol), N-hydroxysuccinimide (53 mg 97%, 0.445 mmol), and dicyclohexylcarbodiimide (88 mg, 0.421 mmol) in dry THF (4 mL) was stirred at room temperature under an atmosphere of argon for 2 h. This solution was directly used for preparation of compound 35.

N-[3-(Benzyloxycarbonylamino)phenylethanoyloxy]succinimide (34)

This active ester was made in a similar way as described for 33 and was directly used for preparation of compound 36.

1-N-[4-(benzyloxycarbonylamino)phenylethanoyl]-6-O-[2-N-[4-(benzyloxycarbonyl)butylamino]ethylamino]-3,2',6'-Tris(N-benzyloxycarbonyl)neamine (35)

To an ice-cold solution of 27 (100 mg, 0.103 mmol) in 2:1 THF-water (3 mL) was added a saturated solution of NaHCO$_3$ (150 µL). To this mixture was added dropwise a solution of the active ester 33 (1.0 mL 0.105 M solution in THE, 0.105 mmol) over 30 min and the reaction mixture was stirred for 1 h at room temperature. Concentration of the mixture gave a solid, which was suspended in water, filtered and washed with water and ether to provide a solid as crude product. The solid was dissolved in MeOH—CH$_2$Cl$_2$, pre-absorbed on silica gel (~1 g), dried and purified on a column (SiO$_2$, 25:1:0.1 to 15:3:0.2 CHCl$_3$/MeOH/NH$_4$OH) to give 35 (115 mg, 74%) as a pure white solid. R$_f$ 0.38 (15:3:0.2 CHCl$_3$/MeOH/NH$_4$OH); mp 232–34° C.; FTIR (KBr): 3315, 3063, 3034, 2944, 1698, 1610, 1533, 1454, 1415, 1228, 1132, 1050, 740, 696 cm$^{-1}$; $^1$H NMR (400 MHz, pyridine-d$_5$) δ 10.83 (s, 1H, ArNHCbz), 8.98 (d, J=6.8 Hz, 1H, NH), 8.29 (d, J=8.4 Hz, 1H, NH), 8.05–8.02 (m, 2H, NH), 7.87 (d, J=8.0 Hz, 2H), 7.83 (s, 1H, NH), 7.56–7.25 (m, 27H), 6.04 (s, 1H, H1'), 5.54 (d, J=12.0 Hz, 1H), 5.35–5.34 (m, 7H), 5.29–5.19 (m, 3H), 4.63 (d, J=8.8 Hz, 1H), 4.52 (t, J=8.0 Hz, 2H), 4.28–4.21 (m, 1H), 4.13–4.07 (m, 4H), 4.07–4.00 (m, 2H), 3.89–3.78 (m, 3H), 3.68 (t, J=10.0 Hz, 1H), 3.36 (d, J=4.0 Hz, 2H), 2.80 (br s, 1H), 2.75–2.65 (m, 2H), 2.44 (d, J=12.4 Hz, 1H, H2$_{eq}$), 1.91 (q, J=12.0 Hz, 1H, H2$_{ax}$), 1.74 (br s, 2H), 1.65 (d, J=6.4 Hz, 2H); $^{13}$C NMR (100 MHz, pyridine-d$_5$) δ 171.2, 157.8, 157.2, 156.8, 154.4, 138.8, 138.1, 138.0, 137.9, 137.5, 131.2, 130.2, 130.1, 128.8, 128.7 (2C), 128.6, 128.4, 128.3, 128.2, 128.1, 128.0, 119.1, 100.4 (C1'), 84.7, 82.8, 77.1, 76.3, 73.0, 72.9, 72.5, 69.7 (CH$_2$), 66.5 (CH$_2$Ph), 66.4 (CH$_2$Ph), 66.3 (CH$_2$Ph), 66.1 (CH$_2$Ph), 57.7, 51.2, 49.5, 49.2 (CH$_2$), 48.7 (CH$_2$), 43.2 (CH$_2$), 42.8 (CH$_2$), 40.9 (CH$_2$), 35.2 (CH$_2$), 27.9 (CH$_2$), 25.9 (CH$_2$); MS (FAB, NBA) 1239 (M$^+$); HRMS (FAB, NBA) calcd for C$_{66}$H$_{78}$N$_7$O$_{17}$ (MH$^+$) 1240.5453. found 1240.5474.

1-N-[4-(benzyloxycarbonylamino)phenylethanoyl]-6-O-[2-N-[4-(benzyloxycarbonyl)butylamino]ethylamino]-3,2',6'-Tris(N-benzyloxycarbonyl)neamine (36)

To an ice-cold solution of 27 (150 mg, 0.154 mmol) in 2:1 THF-water (4.5 mL) was added a saturated solution of NaHCO$_3$ (200 µL) and the mixture was treated with a solution of the active ester 34 (1.5 mL 0.105 M solution in THF, 0.158 mmol) as described for 35. Yield 175 mg, 75%. R$_f$ 0.38 (15:3:0.2 CHCl$_3$/MeOH/NH$_4$OH); mp 223–25° C.; FTIR (KBr): 3318, 3063, 3033, 2941, 1696, 1646, 1539, 1454, 1230, 1132, 1055, 1012, 736, 696 cm$^{-1}$; $^1$H NMR (500 MHz, pyridine-d$_5$) δ 10.93 (s, 1H, ArNHCbz), 8.94 (d, J=8.0 Hz, 1H, NH), 8.32 (d, J=8.5 Hz, 1H, NH), 8.05 (s, 2H), 7.97 (t, J=6.0 Hz, 1H, NH), 7.88 (d, J=8.0 Hz, 1H, NH), 7.80 (s, 1H, NH), 7.56–7.25 (m, 27H), 6.00 (s, 1H, H1'), 5.54 (d, J=12.5 Hz, 1H), 5.38–5.33 (m, 6H), 5.30–5.26 (m, 2H), 5.24–5.19 (m, 2H), 4.63 (d, J=8.5 Hz, 1H), 4.56–4.47 (m, 2H), 4.30 (br s, 1H), 4.14–4.05 (m, 3H), 4.00 (t, J=8.5 Hz, 2H), 3.93 (br s, 1H), 3.87 (t, J=9.0 Hz, 1H), 3.58 (t, J=9.0 Hz, 1H), 3.36 (t, J=6.0 Hz, 2H), 2.71 (br s, 1H), 2.65 (br s, 1H), 2.54–2.47 (m, 2H), 2.41 (d, J=12.5 Hz, 1H, H2$_{eq}$), 1.93 (q, J=12.5 Hz, 1H, H2$_{ax}$), 1.59 (q, J=7.0 Hz, 2H),1.56–1.52 (m, 2H), 1.34–1.28 (m, 1H); $^{13}$C NMR (125 MHz, pyridine-d$_5$) δ 170.7, 157.8, 157.2, 156.8, 154.4, 140.4, 138.2, 138.0, 137.8, 137.7, 137.4, 135.8, 129.3, 128.8, 128.7 (2C), 128.6, 128.4, 128.3, 128.2, 128.1, 128.0, 127.9, 124.0, 123.8, 119.8, 117.3, 100.5 (C1'), 84.8, 83.0, 77.0, 73.1, 72.9, 72.5, 70.9 (CH$_2$), 66.5 (CH$_2$Ph), 66.4 (CH$_2$Ph), 66.3 (CH$_2$Ph), 66.1 (CH$_2$Ph), 57.7, 51.2, 49.9 (CH$_2$), 49.6, 49.2 (CH$_2$), 44.0 (CH$_2$), 42.8 (CH$_2$), 41.2 (CH$_2$), 35.3 (CH$_2$), 28.1 (CH$_2$), 27.0 (CH$_2$); MS (FAB, NBA) 1239 (M$^+$); HRMS (FAB, NBA) calcd for C$_{66}$H$_{78}$N$_7$O$_{17}$ (MH$^+$) 1240.5453. found 1240.5448.

1-N-[4-Aminophenylethanoyl]-6-O-[2-N-(4-butylamino)ethylamino]neamine (8)

To a solution of 35 (28 mg, 0.022 mmol) in glacial acetic acid (400 µL) was added palladium (Pd) on activated carbon (120 mg, 10%). This mixture was treated with 1,4-cyclohexadiene (240 µL, 2.60 mmol) at room temperature under an atmosphere of argon for 4 h. The mixture was diluted with water, filtered (Celite), and the filter cake was thoroughly washed with water. Concentration of the filtrate gave a residue, which was purified on a column (Amberlite CG-50 NH4$^+$ form, 3×1 cm, 0.0–0.8 M aqueous ammonia) to furnish the product as a free base. Treatment of this free base with excess 0.1 N aqueous HCl (1–2 mL) followed by lyophilization of the solution afforded 8 (10 mg, 56%) as a hydrochloride salt. R$_f$ 0.22 (9:4:4 MeOH/H$_2$O/NH$_4$OH); FTIR (KBr): 3419 (br), 2966 (br), 1651, 1599, 1500, 1451, 1118, 1054, 1028, 687, 571 cm$^{-1}$; $^1$H NMR (500 MHz, D$_2$O) δ 7.32–7.18 (m, 4H), 5.74 (d, J=3.5 Hz, 1H, H1'), 3.89–3.79 (m, 3H), 3.78–3.73 (m, 1H), 3.62 (t, J=9.5 Hz, 1H), 3.59–3.55 (m, 1H), 3.52 (s, 2H), 3.35–3.28 (m, 3H), 3.25 (t, J=10 Hz, 1H), 3.13 (q, J=6.5 Hz, 1H), 2.95 (dq, J=13.0, 3.0 Hz, 1H), 2.85 (t, J=7.0 Hz, 4H), 2.71–2.66 (m, 1H), 2.07 (dt, J=13.0, 4.5 Hz, 1H, H2$_{eq}$), 1.64 (q, J=13.0 Hz, 1H, H2$_{ax}$), 1.56 (t, J=3.5 Hz, 2H), 1.42 (s, 2H); $^{13}$C NMR (125 MHz, D$_2$O) δ 173.9, 136.0, 131.0, 129.3, 128.2, 123.5, 115.0, 96.1 (C1'), 83.2, 78.0, 75.8, 75.2, 70.8, 69.3, 68.3, 67.4 (CH$_2$), 53.6, 48.9, 48.2, 47.5 (CH$_2$), 46.9 (CH$_2$), 42.1 (CH$_2$), 40.2 (C6'), 38.9 (CH$_2$), 30.2 (C2), 24.0 (CH$_2$), 22.8 (CH$_2$); MS (FAB, NBA) 569 (M$^+$); HRMS (FAB, NBA) calcd for C$_{26}$H$_{48}$N$_7$O$_7$ (MH$^+$) 570.3591.

1-N-[3-Aminophenylethanoyl]-6-O-[2-N-(4-butylamino)ethylamino]neamine (9)

This compound was prepared from 36 (53 mg, 0.043 mmol) in a similar manner as described for 8 to give the title compound (21 mg, 62%) as a hydrochloride salt. R$_f$ 0.22 (9:4:4 MeOH/H$_2$O/NH$_4$OH); FTIR (KBr): 3419 (br), 2960 (br), 1657, 1631, 1599, 1484, 1451, 1119, 1055, 1029, 687, 524, 453 cm$^{-1}$; $^1$H NMR (400 MHz, D$_2$O) δ 7.48 (t, J=8.0 Hz, 1H), 7.40 (d, J=8.0 Hz, 1H), 7.33 (d, J=10.0 Hz, 2H), 5.86 (d, J=4.0 Hz, 1H, H1'), 3.99–3.92 (m, 4H), 3.84 (t, J=8.0 Hz, 1H), 3.75 (t, J=9.2 Hz, 1H), 3.64 (s, 3H), 3.47–3.34 (m, 5H), 3.23 (dd, J=12.8, 9.2 Hz, 1H), 3.04–2.94 (m, 3H), 2.75–2.70 (m, 1H), 2.19 (dt, J=12.8, 4.8 Hz, 1H, H2$_{eq}$), 1.77 (q, J=12.8 Hz, 1H, H2$_{ax}$), 1.66 (s, 4H); $^{13}$C NMR (100 MHz, D$_2$O) δ 173.8, 137.3, 130.8, 130.1, 124.1, 122.3, 96.1 (C1'), 83.2, 77.5, 75.3, 70.9, 69.4, 68.4, 67.5 (CH$_2$), 53.8, 49.0, 48.3, 47.5 (CH$_2$), 47.0 (CH$_2$), 42.4 (CH$_2$), 40.4 (C6'), 39.1 (CH$_2$), 30.3 (C2), 24.2 (CH$_2$), 22.9 (CH$_2$); MS (FAB, NBA) 569 (M$^+$); HRMS (FAB, NBA) calcd for C$_{26}$H$_{48}$N$_7$O$_7$ (MH$^+$) 570.3611.

The following illustrate representative pharmaceutical dosage forms, containing a compound of the present invention ('Compound X'), for therapeutic, and/or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (viii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (ix) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (x) Injection 1 | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (xi) Injection 2 | mg/mL |
|---|---|
| 'Compound X' | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (xii) Aerosol | mg/can |
|---|---|
| 'Compound X' | 20.0 |
| Oleic acid | 10.0 |

-continued

| | |
|---|---|
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art. Although specific quantities of "Compound X" are shown in the above illustrative examples, it is to be understood that the compounds can be present in any ratio provided the final formulation possesses the desired biological properties.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

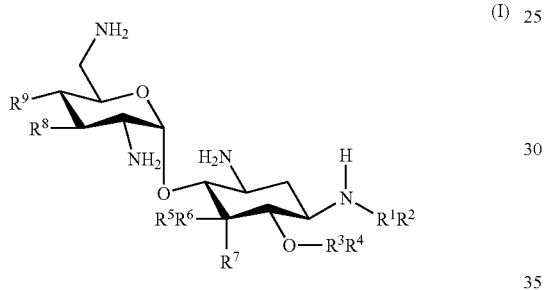

wherein:
R$^1$ is thio, sulfinyl, sulfonyl, a direct bond, or C=X, wherein X is O or S;
R$^2$ is (C$_1$–C$_{12}$)alkyl, (C$_6$–C$_{10}$)aryl (C$_1$–C$_{12}$)alkyl, heteroaryl (C$_1$–C$_{12}$)alkyl, or (C$_3$–C$_8$)cycloalkyl (C$_1$–C$_{12}$) alkyl; wherein any alkyl, aryl, heteroaryl, or cycloalkyl is substituted with one or more amino or hydroxy;
R$^3$ is a direct bond or C=X, wherein X is O or S;
R$^4$ is (C$_1$–C$_{12}$)alkyl optionally substituted with one or more NR$^a$R$^b$, wherein R$^a$ and R$^b$ are each independently hydrogen, (C$_1$–C$_{12}$)alkyl, or (C$_6$–C$_{10}$)aryl (C$_1$–C$_{12}$)alkyl; wherein any alkyl or aryl of R$^4$, R$^a$ or R$^b$ is optionally substituted with one or more amino, hydroxy, or guanidinyl;
R$^5$ is hydroxy, halo, or hydrogen and R$^6$ is a direct bond; or R$^5$ is (C$_1$–C$_{12}$)alkyl optionally substituted with one or more NR$^c$R$^d$, wherein R$^c$ and R$^d$ are each independently hydrogen, (C$_1$–C$_{12}$)alkyl, or (C$_6$–C$_{10}$)aryl (C$_1$–C$_{12}$)alkyl, wherein any alkyl or aryl of R$^5$, R$^c$ or R$^d$ is optionally substituted with one or more amino, hydroxy, or guanidinyl, and R$^6$ is oxy, thio, or C=X, wherein X is O or S;
R$^7$ is hydrogen, halo, or hydroxy;
R$^8$ is hydrogen or hydroxy; and
R$^9$ is hydrogen or hydroxy;
wherein any alkyl is optionally interrupted with one or more oxy, thio, sulfinyl, or sulfonyl; and
wherein any alkyl, aryl, heteroaryl, or cycloalkyl is optionally substituted on carbon with one or more halo, cyano, nitro, trifluoromethyl, hydroxy, (C$_1$–C$_6$)alkoxy, mercapto, oxo, thioxo, or NR$^e$R$^f$, wherein R$^e$ and R$^f$ are each independently hydrogen, (C$_1$–C$_{12}$)alkyl, or (C$_6$–C$_{10}$)aryl (C$_1$–C$_{12}$)alkyl;
or a pharmaceutically acceptable salt thereof.

2. The compound of claim 1 wherein R$^1$ is sulfonyl, a direct bond, or C=X, wherein X is O or S.

3. The compound of claim 1 wherein R$^2$ is (C$_1$–C$_{12}$)alkyl, or (C$_6$–C$_{10}$)aryl (C$_1$–C$_{12}$)alkyl, wherein any alkyl or aryl is substituted with one or more amino and wherein any alkyl is optionally substituted with one or more hydroxy or mercapto.

4. The compound of claim 3 wherein the (C$_1$–C$_{12}$)alkyl is terminally substituted with an amino or the aryl of (C$_6$–C$_{10}$) aryl (C$_1$–C$_{12}$)alkyl is substituted with an amino.

5. The compound of claim 1 wherein R$^1$R$^2$ is a group of the formula:

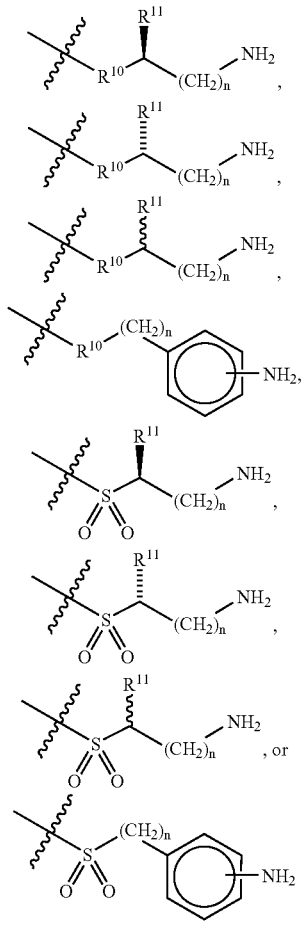

wherein
n is 0 to 6;
R$^{10}$ is sulfinyl, sulfonyl, a direct bond, or C=X wherein X is O or S; and
R$^{11}$ is hydroxy, mercapto, or NR$^g$R$^h$, wherein R$^g$ and R$^h$ are each independently hydrogen, (C$_1$–C$_8$)alkyl, or (C$_6$–C$_{10}$)aryl (C$_1$–C$_8$)alkyl.

6. The compound of claim 1 wherein R$^3$ is a direct bond.

7. The compound of claim 1 wherein R$^3$ is C=X, wherein X is S or O.

8. The compound of claim 1 wherein R$^4$ is (C$_1$–C$_{12}$)alkyl substituted with one or more NR$^a$R$^b$, wherein R$^a$ and R$^b$ are each independently hydrogen, (C$_1$–C$_{12}$)alkyl, or (C$_6$–C$_{10}$)

aryl ($C_1$–$C_{12}$)alkyl; wherein any alkyl is optionally substituted with one or more hydroxy or mercapto.

9. The compound of claim 1 wherein $R^4$ is ($C_1$–$C_{12}$)alkyl substituted with one or more $NR^aR^b$, wherein $R^a$ and $R^b$ are each independently hydrogen, ($C_1$–$C_{12}$)alkyl, or ($C_6$–$C_{10}$)aryl ($C_1$–$C_{12}$)alkyl; wherein any alkyl or aryl of $R^4$, $R^a$ or $R^b$ is substituted with one or more amino or guanidinyl.

10. The compound of claim 1 wherein $R^3R^4$ is a group of the formula:

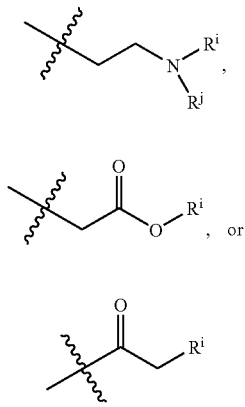

wherein
$R^i$ is hydrogen,

$R^j$ is

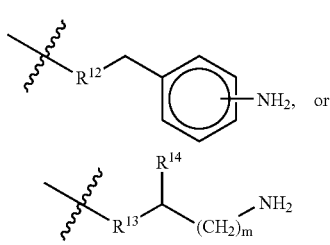

wherein
$R^{12}$ is sulfinyl, sulfonyl, a direct bond, or C=X, wherein X is S or O;
$R^{13}$ is sulfinyl, sulfonyl, a direct bond, or C=X, wherein X is S or O;
$R^{14}$ is hydrogen, hydroxy, mercapto, or $NR^iR^j$, wherein $R^i$ and $R^j$ are each independently hydrogen, ($C_1$–$C_8$)alkyl, or ($C_6$–$C_{10}$)aryl($C_1$–$C_8$)alkyl; and
m is 0 to 8.

11. The compound of claim 10 wherein $R^i$ is $(CH_2)_n$—$NH_2$, wherein n is 2 to 8; or $R^i$ is guanidinyl.

12. The compound of claim 10 wherein $R^j$ is a group of the formula:

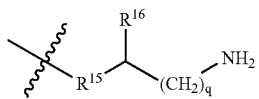

wherein
$R^{15}$ is C=X, wherein X is O or S;
$R^{16}$ is hydrogen, hydroxy or amino; and
q is 2.

13. The compound of claim 1 wherein $R^5$ is hydroxy, halo, or hydrogen and $R^6$ is a direct bond.

14. The compound of claim 1 wherein $R^5$ is ($C_1$–$C_{12}$)alkyl optionally substituted with one or more oxo or $NR^mR^n$, wherein $R^m$ and $R^n$ are each independently hydrogen, ($C_1$–$C_{12}$)alkyl, or ($C_6$–$C_{10}$)aryl ($C_1$–$C_{12}$)alkyl, wherein any alkyl or aryl of $R^5$, $R^m$ or $R^n$ is optionally substituted with one or more amino or guanidinyl, and $R^6$ is oxy, thio, or C=X, wherein X is O or S.

15. The compound of claim 1 wherein $R^5R^6$ is hydrogen, hydroxy, flouro, or a group of the formula:

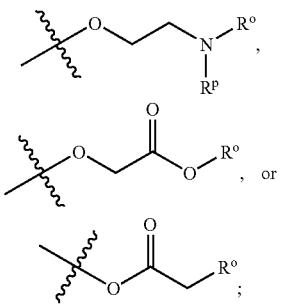

wherein
$R^o$ is hydrogen,

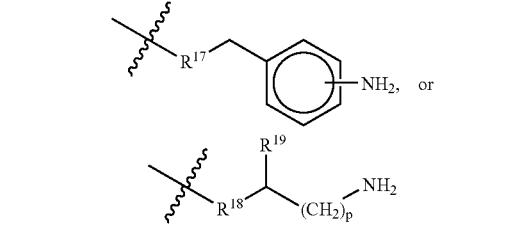

$R^p$ is wherein
$R^{17}$ is sulfinyl, sulfonyl, a direct bond, or C=X, wherein X is S or O;

R¹⁸ is sulfinyl, sulfonyl, a direct bond, or C=X, wherein X is S or O;
R¹⁹ is hydrogen, hydroxy, mercapto, or NR$^q$R$^s$, wherein R$^q$ and R$^s$ are each independently hydrogen, (C₁–C₈)alkyl, or (C₆–C₁₀)aryl(C₁–C₈)alkyl; and
p is 0 to 6.

16. The compound of claim 1 wherein R⁵R⁶ is hydroxy.
17. The compound of claim 1 wherein R⁷ is hydrogen, fluoro, or hydroxy.
18. The compound of claim 1 wherein R⁷ is hydrogen.
19. The compound of claim 1 wherein R⁸ is hydrogen.
20. The compound of claim 1 wherein R⁸ is hydroxy.
21. The compound of claim 1 wherein R⁹ is hydrogen.
22. The compound of claim 1 wherein R⁹ is hydroxy.
23. The compound of claim 1 which is or a pharmaceutically acceptable salt thereof.
24. The compound of claim 1 which is or a pharmaceutically acceptable salt thereof.
25. The compound of claim 1 which is or a pharmaceutically acceptable salt thereof.

26. The compound of claim 1 which is or a pharmaceutically acceptable salt thereof.
27. The compound of claim 1 which is

or a pharmaceutically acceptable salt thereof.
28. The compound or a pharmaceutically acceptable salt thereof.

29. The compound of claim 1 which is

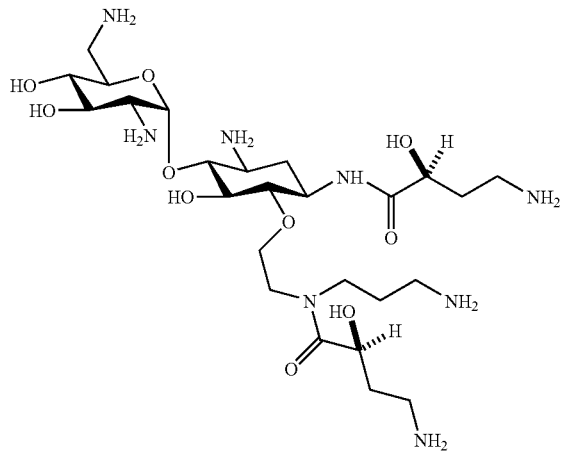

or a pharmaceutically acceptable salt thereof.

30. The compound of claim 1 which is

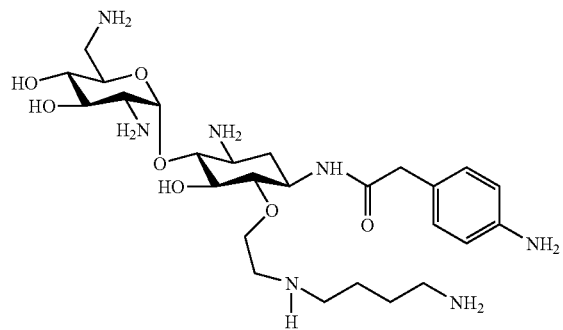

or a pharmaceutically acceptable salt thereof.

31. The compound of claim 1 which is or a pharmaceutically acceptable salt thereof.

32. A pharmaceutical composition comprising a compound of claim 1 and a pharmaceutically acceptable carrier or diluent.

33. The pharmaceutical composition of claim 32 further comprising one or more antibiotic agents chosen from cephalosporin, penicillin, tetracycline, neamine, amikacin, paromomycin, kanamycin, or a combination thereof.

34. A method for treating a bacterial infection in a mammal comprising administering to the mammal in need of such prevention or treatment a compound of claim 1.

35. The method of claim 34 further comprising administering one or more antibiotic agents chosen from cephalosporin, penicillin, tetracycline, neamine, amikacin, paromomycin, kanamycin, or a combination thereof.

36. The method of claim 34 wherein the mammal is a human.

* * * * *